(12) United States Patent
Kalish et al.

(10) Patent No.: US 9,156,804 B2
(45) Date of Patent: Oct. 13, 2015

(54) NITROXYL DONORS WITH IMPROVED THERAPEUTIC INDEX

(71) Applicant: Cardioxyl Pharmaceuticals, Inc., Chapel Hill, NC (US)

(72) Inventors: Vincent Jacob Kalish, Annapolis, MD (US); Frederick Arthur Brookfield, Abingdon (GB); Stephen Martin Courtney, Abingdon (GB); Lisa Marie Frost, Abingdon (GB); John P. Toscano, Glen Arm, MD (US)

(73) Assignee: Cardioxyl Pharmaceuticals, Inc., Chapel Hill, NC (US)

( * ) Notice: Subject to any disclaimer, the term of this patent is extended or adjusted under 35 U.S.C. 154(b) by 0 days.

(21) Appl. No.: 14/641,377

(22) Filed: Mar. 7, 2015

(65) Prior Publication Data

US 2015/0175566 A1   Jun. 25, 2015

Related U.S. Application Data

(63) Continuation of application No. 14/158,456, filed on Jan. 17, 2014, now Pat. No. 8,987,326.

(60) Provisional application No. 61/754,237, filed on Jan. 18, 2013, provisional application No. 61/782,781, filed on Mar. 14, 2013.

(51) Int. Cl.
| | |
|---|---|
| A61K 31/341 | (2006.01) |
| A61K 31/18 | (2006.01) |
| C07D 307/64 | (2006.01) |
| C07C 317/14 | (2006.01) |

(52) U.S. Cl.
CPC .............. *C07D 307/64* (2013.01); *A61K 31/18* (2013.01); *A61K 31/341* (2013.01); *C07C 317/14* (2013.01)

(58) Field of Classification Search
USPC .......................................... 514/471; 549/479
See application file for complete search history.

(56) References Cited

U.S. PATENT DOCUMENTS

| | | | |
|---|---|---|---|
| 3,751,255 | A | 8/1973 | Wilson et al. |
| 4,369,174 | A | 1/1983 | Nagai et al. |
| 4,539,321 | A | 9/1985 | Campbell |
| 4,663,351 | A | 5/1987 | Diamond |
| 4,798,824 | A | 1/1989 | Belzer et al. |
| 4,842,866 | A | 6/1989 | Horder et al. |
| 5,217,720 | A | 6/1993 | Sekigawa et al. |
| 6,525,081 | B1 | 2/2003 | Matsumoto et al. |
| 6,569,457 | B2 | 5/2003 | Ullah et al. |
| 6,638,534 | B1 | 10/2003 | Ishibashi et al. |
| 6,936,639 | B2 | 8/2005 | Wink et al. |
| 7,696,373 | B2 | 4/2010 | King |
| 7,863,262 | B2 | 1/2011 | Wink et al. |
| 8,030,356 | B2 | 10/2011 | Toscano et al. |
| 8,227,639 | B2 | 7/2012 | Toscano et al. |
| 8,268,890 | B2 | 9/2012 | Wink et al. |
| 8,318,705 | B2 | 11/2012 | Frost et al. |
| 8,674,132 | B2 | 3/2014 | Toscano et al. |
| 2004/0038947 | A1 | 2/2004 | Wink et al. |
| 2005/0153966 | A1 | 7/2005 | Gangloff et al. |
| 2005/0192254 | A1 | 9/2005 | Wink et al. |
| 2009/0163487 | A1 | 6/2009 | Toscano et al. |
| 2009/0186045 | A1 | 7/2009 | Ray et al. |
| 2009/0281067 | A1 | 11/2009 | Toscano, III et al. |
| 2009/0298795 | A1 | 12/2009 | Paolocci et al. |
| 2011/0136827 | A1 | 6/2011 | Toscano et al. |
| 2011/0144067 | A1 | 6/2011 | Toscano et al. |
| 2011/0306614 | A1 | 12/2011 | Toscano et al. |
| 2012/0201907 | A1 | 8/2012 | Wink et al. |
| 2014/0194416 | A1 | 7/2014 | Toscano et al. |

FOREIGN PATENT DOCUMENTS

| | | |
|---|---|---|
| EP | 1219306 A1 | 7/2002 |
| JP | H-221371 A | 9/1989 |
| JP | H-221372 A | 9/1989 |
| JP | 04-321671 A | 11/1992 |
| JP | 10-142729 A | 5/1998 |
| JP | 2002-072459 | 3/2002 |
| SU | 186456 | 10/1966 |
| WO | WO 01/10827 A1 | 2/2001 |
| WO | WO 02/100810 A1 | 12/2002 |
| WO | WO 2005/074598 A2 | 8/2005 |
| WO | WO 2006/086188 A2 | 8/2006 |
| WO | WO 2007/002444 A1 | 1/2007 |
| WO | WO 2007/109175 A1 | 9/2007 |
| WO | WO 2009/042970 A1 | 4/2009 |

(Continued)

OTHER PUBLICATIONS

Abdellatif et al., "Synthesis of New 1-[4-Methane(amino)sulfonylphenyl)]-5-[4-(aminophenyl)]-3-trifluoromethyl-1H-pyrazoles," *J. Heterocyclic Chem.*, 45:1707-1710 (2008).

Andrewes et al., "Experimental Chemotherapy of Typhus: Anti-Rickettsial Action of p-Sulphonamidobenzamidine and Related Compounds," *Proc. R. Soc. Lond., B, Biol. Sci.*, 133(1):20-62 (1946).

Backx et al., "The Relationship between Contractile Force and Intracellular [$Ca^{2+}$] in Intact Rat Cardiac Trabeculae," *J. Gen. Physiol.*, 105:1-19 (1995).

Badesch et al., "Diagnosis and Assessment of Pulmonary Arterial Hypertension," *J. Amer. College Cardiology*, 54(1, Suppl S):S55-S66( 2009).

Baerlocher et al., "Few and More Potent Antifungal Disulfides," *Aust. J. Chem.*, 53(1):1-5 (2000).

(Continued)

*Primary Examiner* — Kristin Vajda
(74) *Attorney, Agent, or Firm* — Byrne Poh LLP; Nina R. Horan

(57) ABSTRACT

The disclosed subject matter provides N-substituted hydroxylamine derivative compounds, pharmaceutical compositions and kits comprising such compounds, and methods of using such compounds or pharmaceutical compositions. In particular, the disclosed subject matter provides methods of using such compounds or pharmaceutical compositions for treating heart failure.

26 Claims, 5 Drawing Sheets

(56) References Cited

FOREIGN PATENT DOCUMENTS

WO   WO 2011/063339 A1   5/2011
WO   WO 2014/113700 A1   7/2014

OTHER PUBLICATIONS

Baumgarth et al., "(2-Methyl-5-(methylsulfonyl)benzoyl)guanidine Na'/H+ Antiporter Inhibitors," *J. Med. Chem.*, 40(13):2017-2034 (1997).
Bazylinski et al., "Metmyoglobin and Methemoglobin as Efficient Traps for Nitrosyl Hydride (Nitroxyl) in Neutral Aqueous Solution," *J. Amer. Chem. Soc.*, 107(26):7982-7986 (1985).
Bhardwaj et al., "A diazen-1-ium-1,2-diolate analog of 7-azabenzobicyclo[2.2.1] heptanes: Synthesis, nitric oxide and nitroxyl release, in vitro hemodynamic, and anti-hypertensive studies," *Bioorg. Med. Chem. Lett.*, 23:2769-2774 (2013).
Bonner et al., "Kinetic, Isotopic, and $^{15}$N NMR Study of N-Hydroxybenzenesulfonamide Decomposition: An HNO Source Reaction," *Inorg. Chem.*, 31:2514-2519 (1992).
Bouzamondo et al., "Beta-blocker treatment in heart failure," *Fundamental Clinical Pharmacol.*, 15:95-109 (2001).
Bristow et al., "Inotropes and β-Blockers: Is There a Need for New Guidelines?," *J. Cardiac Failure*, 7(2)(Suppl 1):8-12 (2001).
Byrnes et al., "Potential Antitumor Agents via Inhibitors of L-Asparagine Synthetase: Substituted Sulfonamides and Sulfonyl Hydrazides Related to Glutamine," *J. Pharm. Sci.*, 67(11):1550-1553 (1978).
Byrnes et al., "Potential Inhibitors of L-Asparagine Biosynthesis. 4. Substituted Sulfonamide and Sulfonylhydrazide Analogues of L-Asparagine," *J. Med. Chem.*, 21(1):45-49 (1978).
Caplus (Mar. 12, 2002) Accession No. 2002:176265, Japanese Patent Publication No. 2002-072459-A, one page.
Chemcats (Jan. 17, 2008) Accession No. 2033522701, Enamine Building Blocks Enamine: Kiev, UK, one page.
Chemcats (Jan. 17, 2008) Accession No. 2033715491, Enamine Screening Library Enamine: Kiev, UK, one page.
Chemcats (Jun. 13, 2008) Accession No. 2037996565, Aurora Screening Library, Aurora Fine Chemicals, LLC: San Diego, CA, one page.
Chowdhury et al., "Synthesis of new 4-[2-methyl(amino)sulfonylphenyl)-5-trifluoromethyl-2H-pyrazol-3-yl]-1,2,3,6-tetrahydropyridines: A search for novel nitric oxide donor anti-inflammatory agents," *Bioorg. Med. Chem.*, 16:8882-8888 (2008).
Chowdhury et al., "Celecoxib analogs possessing a N-(4-nitrooxybutyl)piperidin-4-yl or N-(4-nitroxybutyl)-1,2,3,6-tetrahydropyridin-4-yl nitric oxide donor moiety: Synthesis, biological evaluation and nitric oxide release studies," *Bioorg. Med. Chem. Lett.*, 20:1324-1329 (2010).
Communication issued on Apr. 9, 2013, in European Patent Application No. 12155608.8.
Communication issued on Aug. 8, 2013, in European Patent Application No. 12155608.8.
Crawford et al., "Hypoxia, red blood cells, and nitrite regulate NO-dependent hypoxic vasodilation," *Blood*, 107(2):566-575 (2006).
Database CAPlus Abstract Accession No. 1994:645157, Chemical Abstracts Service, Columbus, Ohio (1994).
Examination Report issued on Jun. 14, 2011, in Australian Patent Application No. 2007227457.
Examination Report issued on Nov. 22, 2010, in European Patent Application No. 07753345.3.
Examination Report issued on Apr. 14, 2010, in New Zealand Patent Application No. 570971.
Examination Report issued on Aug. 25, 2011, in New Zealand Patent Application No. 570971.
Examination Report issued on Nov. 23, 2010, in New Zealand Patent Application No. 584036.
Examination Report issued on Oct. 21, 2011, in New Zealand Patent Application No. 595770.
Extended Search Report and Written Opinion issued on Jul. 13, 2012, in European Patent Application No. 12155608.8.
Extended Search Report issued on Apr. 5, 2013, in European Patent Application No. 12195114.9.
Extended Search Report issued on Apr. 5, 2013, in European Patent Application No. 12195118.0.
Extended Search Report issued on Apr. 5, 2013, in European Patent Application No. 12195124.8.
Extended Search Report issued on Apr. 5, 2013, in European Patent Application No. 12195128.9.
Fukuto et al., "The Physiological Chemistry and Biological Activity of Nitroxyl (HNO): The Neglected, Misunderstood, and Enigmatic Nitrogen Oxide," *Chem. Res. Toxicol.*, 18:790-801 (2005).
Gao et al., "Myofilament $Ca^{2+}$ Sensitivity in Intact Versus Skinned Rat Ventricular Muscle," *Circ. Res.*, 74:408-415 (1994).
Gao et al., "Calcium cycling and contractile activation in intact mouse cardiac muscle," *J. Physiol.*, 507(1):175-184 (1998).
Hare et al., "Nitric Oxide Inhibits the Positive Inotropic Response to β-Adrenergic Stimulation in Humans With Left Ventricular Dysfunction," *Circulation*, 92:2198-2203 (1995).
Hare et al., "Pertussis Toxin-sensitive G Proteins Influence Nitric Oxide Synthase III Activity and Protein Levels in Rat Heart," *J. Clin. Invest.*, 101(6):1424-1431 (1998).
Hart et al., "Differential effects of natriuretic peptides and NO on LV function in heart failure and normal dogs," *Amer. J. Physiol. Heart Circ. Physiol.*, 281:146-154 (2001).
Ingall, "Preventing ischemic stroke," *Postgrad. Med.*, 107(6):34-50 (2000).
International Preliminary Report on Patentability mailed on Sep. 23, 2008, in International Application No. PCT/US2007/006710.
International Search Report mailed on Aug. 22, 2007, in International Application No. PCT/US2007/006710.
International Search Report mailed on Jan. 23, 2009, in International Application No. PCT/US2008/078024.
International Search Report and Written Opinion mailed on Mar. 14, 2014, in International Application No. PCT/US2014/012085 (9 pages).
Jackman et al., "Studies in the Field of Diuretic Agents: Part VIII. Some Miscellaneous Derivatives," *J. Pharmacy Pharmacol.*, 15:202-211 (1963).
Katori et al., "Calcitonin Gene-Related Peptide In Vivo Positive Inotropy is Attributable to Regional Sympatho-Stimulation and is Blunted in Congestive Heart Failure," *Circ. Res.*, 96:234-243 (2005).
Lee et al., "N-Hydrobenezenecarboximidic Acid Derivatives: A New Class of Nitroxyl-Generating Prodrugs," *Nitric Oxide: Biol. Chem.*, 5(3):278-287 (2001).
Li et al.,"Developing Early Formulations: Practice and Perspective," *Int'l J. Pharmaceutics*, 341(1-2):1-19 (2007).
Lowes et al., "Inotropes in the Beta-Blocker Era," *Clin. Cardiol.*, 23:II-11-III-16 (2000).
Ma et al., "Opposite effects of nitric oxide and nitroxyl on postischemic myocardial injury," *PNAS*, 96(25):14617-14622 (1999).
Mincione et al., "Carbonic Anhydrase Inhibitors: Inhibition of Isozymes, I, II and IV with N-Hydroxysulfonamides—A Novel Class of Intraocular Pressure Lowering Agents," *J. Enzyme Inhibition*, 13:267-284 (1998).
Miranda et al., "Mechanism of Aerobic Decomposition of Angeli's Salt (Sodium Trioxodinitrate) at Physiological pH," *J. Amer. Chem. Soc.*, 127(2):722-731 (2005).
Miranda et al., "Donors of HNO," *Current Topics Med. Chem.*, 5:649-664 (2005).
Nagasawa et al., "Prodrugs of Nitroxyl as Potential Aldehyde Dehydrogenase Inhibitors vis-à-vis Vascular Smooth Muscle Relaxants," *J. Med. Chem.*, 38:1865-1871 (1995).
Nairn, "Solutions, Emulsions, Suspensions and Extracts," pp. 721-752 in *Remington: The Science and Practice of Pharmacy*, 20th Ed. (Lippincott Williams & Wilkins, Baltimore, MD, 2000).
Notice of Allowance issued on Jun. 23, 2014, in U.S. Appl. No. 14/045,404.
Notice of Allowance issued on Sep. 4, 2014, in U.S. Appl. No. 14/045,404.

(56) References Cited

OTHER PUBLICATIONS

Office Action issued on Apr. 10, 2013, in Canadian Patent Application No. 2,645,988.
Office Action issued on May 12, 2010, in Chinese Patent Application No. 200780011079.6.
Office Action issued on Jul. 13, 2011, in Chinese Patent Application No. 200780011079.6.
Office Action issued on May 18, 2012, in Chinese Patent Application No. 200780011079.6.
Office Action issued on Jun. 11, 2014, in Chinese Patent Application No. 201310086960.X.
Office Action issued on May 11, 2011, in Israeli Patent Application No. 193839.
Office Action issued on Sep. 24, 2012, in Israeli Patent Application No. 217739.
Office Action issued on Jun. 16, 2014, in Israeli Patent Application No. 217739.
Office Action issued on Aug. 21, 2012, in Japanese Patent Application No. 2009-500519.
Office Action issued on Jun. 4, 2013, in Japanese Patent Application No. 2009-500519.
Office Action issued on Jun. 10, 2014, in Japanese Patent Application No. 2013-032658.
Office Action issued on Sep. 12, 2013, in Korean Patent Application No. 10-2008-7025245 (with English translation).
Office Action issued on Jul. 23, 2014, in Korean Patent Application No. 10-2008-7025245 (with English translation).
Office Action issued on Jun. 5, 2014, in Korean Patent Application No. 10-2014-7006611 (with English translation).
Office Action issued on Feb. 11, 2011, in Russian Patent Application No. 2008141151/04.
Office Action issued on Sep. 22, 2011, in U.S. Appl. No. 12/239,705.
Office Action issued on Mar. 20, 2014, in U.S. Appl. No. 14/045,404.
Paolocci, "Positive inotropic and lusitropic effects of HNO/NO⁻ in failing hearts: Independence from β-adrenergic signaling," *PNAS*, 100(9):5537-5542 (2003).
Paolocci et al., "cGMP-independent inotropic effects of nitric oxide and peroxynitrite donors: potential role for nitrosylation," *Amer. J. Physiol. Circ. Physiol.*, 279:111982-111988 (2000).
Park et al., "Discovery of an Orally Bioavailable Small Molecule Inhibitor of Prosurvival B-Cell Lymphoma 2 Proteins," *J. Med. Chem.*, 51(21):6902-6915 (2008).
Rastaldo et al., "Cytochrome P-450 metabolite of arachidonic acid mediates bradykinin-induced negative inotropic effect," *Amer. J. Physiol. Circ. Physiol.*, 280:H2823-H2832 (2001).
Registry (Nov. 30, 2004) Accession No. 790725-76-7, one page.
Registry (Feb. 13, 2007) Accession No. 920663-30-5, one page.
Registry (Apr. 13, 2007) Accession No. 930060-34-7, one page.
Rehse et al., "New NO Donors with Antithrombotic and Vasodilating Activities, Part 25, Hydroxylamine Derivatives," *Arch. Pharm. Med. Chem.*, 331:365-367 (1998).

Sabbah et al., "Nitroxyl (HNO) A Novel Approach for the Acute Treatment of Heart Failure," *Circ. Heart Fail.*, 6:1250-1258 (2013) with supplemental material pp. 1-19.
Scozzafava et al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II, and IV, and N-Hydroxysulfonamides Inhibit Both These Zinc Enzymes," *J. Med. Chem.*, 43:3677-3687 (2000).
Scozzafava el al., "Carbonic Anhydrase and Matrix Metalloproteinase Inhibitors: Sulfonylated Amino Acid Hydroxamates with MMP Inhibitory Properties Act as Efficient Inhibitors of CA Isozymes I, II and IV, and N-Hydroxysulfonamides Inhibit Both These Zinc Enzymes," *J. Med. Chem.*, 44:1016 (2001) [errata for C85].
Sha et al., "Hydrolysis of Acyloxy Nitroso Compounds Yields Nitroxyl," *J. Amer. Chem. Soc.*, 128:9687-9692 (2006).
Shami et al., "JS-K, a Glutathione/GlutathioneS-Transferase-activated Nitric Oxide Donor of the Diazeniumdiolate Class with Potent Antineoplastic Activity," *Mol. Cancer Therapeutics*, 2:409-417 (2003).
Singapore Search Report and Written Opinion issued on Jan. 4, 2010, in Singapore Patent Application No. 200806554-2.
Singapore Search Report and Written Opinion issued on Aug. 26, 2011, in Singapore Patent Application No. 201001904-1.
Sirsalmath et al., "The pH of HNO Donation is Modulated by Ring Substitutes in Piloty's Acid Derivatives: Azanone Donors at Biological pH," *J. Inorg. Biochem.*, 118:134-139 (2013).
Slotwiner-Nie et al., "Infectious Diarrhea in the Elderly," *Gastroenterology Clinics of North America*, 30(3):625-635 (2001).
Sutton et al., "Optimization of HNO Production from N,O-bis-Acylated Hydroxylamine Derivatives," *Org. Lett.*, 14(2):472-475 (2012) with supporting information pp. S1-S171.
Suzuki et al., "Novel Inhibitors of Human Histone Deacetylases: Design, Synthesis, Enzyme Inhibition and Cancer Cell Growth Inhibition of SAHA-Based Nonhydroxamates," *J. Med. Chem.*, 48(4):1019-1032 (2005).
Takahira et al., "Dexamethasone Attenuates Neutrophil Infiltration in the Rat Kidney in Ischemia/Reperfusion Injury: The Possible Role of Nitroxyl," *Free Radical Biol. Med.*, 31(6):809-815 (2001).
Thevis et al., "High speed determination of beta-receptor blocking agents in human urine by liquid chromatography/tandem mass spectrometry," *Biomedical Chromatography*, 15:393-402 (2001).
USPTO Official Gazette notice of Reissue Applications Filed dated Dec. 17, 2013.
Written Opinion mailed on Jan. 23, 2009, in International Application No. PCT/US2008/078024.
Wrobel et al., "Synthesis of (bis)Sulfonic Acid, (bis)Benzamides as Follicle-Stimulating Hormone (FSH) Antagonists," *Bioorg. Med. Chem.*, 10:639-656 (2002).
Zamora et al., "Oxidative release of nitric oxide accounts for guanylyl cyclase stimulating, vasodilator and anti-platelet activity of Piloty's acid: a comparison with Ageli's salt," *Biochem. J.*, 312:333-339 (1995).
Zani et al., "Antimicrobial and Genotoxic Properties of Quinoline Derivatives," *Bollettino Chimico Farmaceutico*, 133(5):328-338 (1994).

NITROXYL DONORS WITH IMPROVED THERAPEUTIC INDEX

1. BACKGROUND

Nitroxyl (HNO) has been shown to have positive cardiovascular effects in in vitro and in vivo models of failing hearts. However, at physiological pH, nitroxyl dimerizes to hyponitrous acid, which subsequently dehydrates to nitrous oxide; due to this metastability, nitroxyl for therapeutic use must be generated in situ from donor compounds. A variety of compounds capable of donating nitroxyl have been described and proposed for use in treating disorders known or suspected to be responsive to nitroxyl. See, e.g., U.S. Pat. Nos. 6,936,639; 7,696,373; 8,030,356; 8,268,890; 8,227,639; and 8,318,705 and U.S. pre-grant publication nos. 2009/0281067; 2009/0298795; 2011/0136827; and 2011/0144067. Although all of these compounds are capable of donating nitroxyl, they differ in various physicochemical properties, and there remains a need to identify nitroxyl donors that have physicochemical properties best suited for treating specific clinical conditions via specific routes of administration.

U.S. Pat. No. 8,030,056 describes the synthesis of derivatives of Piloty's acid type compounds that are capable of donating nitroxyl under physiological conditions and are useful in treating heart failure and ischemia/reperfusion injury. The nitroxyl donor CXL-1020 (N-hydroxy-2-methanesulfonylbenzene-1-sulfonamide) has been evaluated in a Phase I safety study in healthy volunteers and in a Phase IIa placebo-controlled, double-blind, dose-escalation study conducted at multiple hospitals. Sabbah et al., "Nitroxyl (HNO) a novel approach for the acute treatment of heart failure", *Circ Heart Fail.*, published online Oct. 9, 2013 (Online ISSN: 1941-3297, Print ISSN: 1941-3289). The studies demonstrated that in patients with systolic heart failure, CXL-1020, when administered intravenously as an aqueous solution at pH=4, reduced both left and right heart filling pressures and systemic vascular resistance, while increasing cardiac and stroke volume index. Hence, the studies demonstrated that CXL-1020 enhances myocardial function in human patients suffering from heart failure. However, at threshold doses of CXL-1020 needed to produce hemodynamic effects, the compound was found to induce side effects including unacceptable levels of inflammatory irritation at and distal to the intravenous insertion site, and the authors report that because of such side effects, this compound would not be a viable candidate for a human therapeutic.

Accordingly, there is a need to develop new nitroxyl donating compounds and compositions that are useful for the treatment of heart failure and that have a suitable toxicological profile. Development of such compounds requires an understanding of the pharmacokinetic profile associated with nitroxyl donation and the factors influencing the toxicological profile. Failure to understand these factors has hampered the development of nitroxyl donating compounds for clinical use.

Moreover, formulating nitroxyl donating compounds has proven to be a considerable challenge. Many of the current nitroxyl donors are insoluble in aqueous solutions and/or are insufficiently stable. Solubility and stability problems often preclude the use of such compounds in pharmaceutical compositions for parenteral and/or oral administration. Accordingly, there exists a need to develop compositions containing nitroxyl donating compounds for parenteral and/or oral administration that are sufficiently stable and have favorable pharmacological and toxicological profiles.

Citation of any reference in Section 1 of this application is not to be construed as an admission that such reference is prior art to the present application.

2. SUMMARY OF THE DISCLOSURE

The present disclosure relates to the discovery of nitroxyl donating compounds that are highly efficacious in treating cardiovascular diseases (e.g., heart failure) and have a suitable toxicological profile.

In a particular embodiment, a nitroxyl donating compound of the disclosure is a compound of the formula (1):

(1)

In another embodiment, a nitroxyl donating compound of the disclosure is a compound of the formula (2):

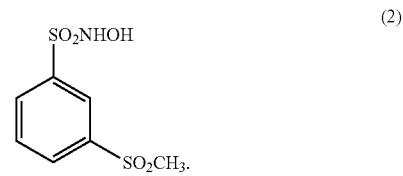

(2)

In another embodiment, the disclosure provides compounds of the formula (3):

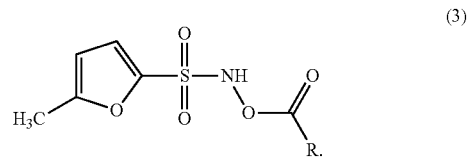

(3)

wherein R is hydrogen, —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —$NH_2$, —NH—$(C_1-C_4)$alkyl, or —N$((C_1-C_4)$alkyl$)_2$, wherein said —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —NH—$(C_1-C_4)$alkyl, or —N$((C_1-C_4)$alkyl$)_2$ can be unsubstituted or substituted with one or more substituents selected from halo, —$(C_1-C_6)$alkyl, —$(C_2-C_4)$alkenyl, —$(C_2-C_3)$alkynyl, -(5- or 6-membered)heteroaryl, —O—$(C_1-C_6)$alkyl, —S—$(C_1-C_6)$alkyl, —C(halo)$_3$, —CH(halo)$_2$, —$CH_2$(halo), —CN, —$NO_2$, —$NH_2$, —NH—$(C_1-C_4)$alkyl, —N(—$(C_1-C_4)$alkyl)$_2$, —C(=O)$(C_1-C_4)$alkyl, —C(=O)O$(C_1-C_4)$alkyl, —OC(=O)$(C_1-C_4)$alkyl, —OC(=O)$NH_2$, —S(=O)$(C_1-C_4)$alkyl, or —S(=O)$_2(C_1-C_4)$alkyl. In particular embodiments, R is methyl, ethyl, benzyl, or phenyl. In particular embodiments, R is methyl or ethyl. In particular embodiments, R is methyl. In particular embodiments, R is ethyl. In particular embodiments, R is benzyl or phenyl. In particular embodiments, R is benzyl. In particular embodiments, R is phenyl.

In another embodiment, the disclosure provides compounds of formula (4):

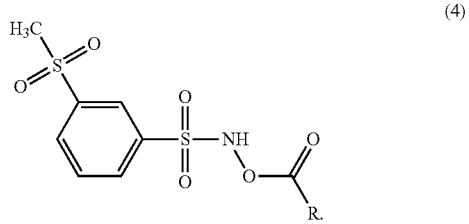

wherein R and its embodiments are as defined above with respect to the compound of formula (3).

Compounds of the disclosure have or are believed to have a highly favorable therapeutic index. In particular, compounds of formula (1) and formula (2) have both desirable hemodynamic profiles and toxicological profiles. The toxicological profile of the compounds of formula (1) and formula (2) is significantly improved relative to the clinical candidate CXL-1020. It has been discovered that the favorable toxicological profile of the compounds of formula (1) and formula (2) stems in part from the half-lives of the compounds, and the discovery of an optimal range of half-lives for such nitroxyl donors. The compound of formula (1) has a half-life of approximately 68 minutes when measured in an aerated phosphate buffered saline (PBS) solution at a pH of 7.4, and approximately 65 minutes when measured in human plasma at a pH of 7.4 in the presence of an anticoagulant (e.g., heparin or sodium citrate), each measured under conditions specified in Example 4. The compound of formula (2) has a half-life of approximately 50 minutes when measured in an aerated phosphate buffered saline (PBS) solution at a pH of 7.4, and approximately 37 minutes when measured in human plasma at a pH of 7.4 in the presence of an anticoagulant (e.g., heparin or sodium citrate), each measured under conditions specified in Example 4.

Moreover, compounds of formula (1) and formula (2) are stable in aqueous solutions and are highly water soluble; they are, thus, amenable to both parenteral and oral administration. The compound of formula (1) has an equilibrium solubility in water of greater than 100 mg/mL while the compound of formula (2) has an equilibrium solubility in water of approximately 10 mg/mL (e.g., under conditions specified in Example 5).

Compounds of the disclosure can be used to treat a variety of conditions that are responsive to nitroxyl therapy. For instance, a nitroxyl donating compound of the disclosure can be used to treat or prevent the occurrence of cardiovascular diseases. In particular embodiments, a nitroxyl donating compound of the disclosure can be used to treat cardiovascular disease, ischemia/reperfusion injury, pulmonary hypertension or another condition responsive to nitroxyl therapy. In other embodiments, a nitroxyl donating compound of the disclosure can be used to treat heart failure. In a particular embodiment, a compound of the disclosure can be used to treat decompensated heart failure (e.g., acute decompensated heart failure). In certain embodiments, the compounds of the disclosure can be used to treat systolic heart failure. In particular embodiments, the compounds of the disclosure can be used to treat diastolic heart failure.

In one aspect, the compounds of the disclosure can be administered via parenteral (e.g., subcutaneous, intramuscular, intravenous or intradermal) administration. The compounds of the disclosure do not induce undesirable local side effects (e.g., irritation and/or inflammation) during or after parenteral administration at doses capable of providing a desired level of efficacy.

In embodiments in which a compound of the disclosure is administered parenterally, it is generally administered as an aqueous solution or suspension. The aqueous solution or suspension can have a pH of from about 4 to about 6.5. In particular embodiments, a compound of the disclosure can be formulated for parenteral injection at a pH of from about 4 to about 5. In other embodiments, a compound of the disclosure can be formulated for parenteral injection at a pH of from about 5 to about 6. In some embodiments, the formulation for parenteral administration can include a stability enhancing agent.

When administered parenterally (e.g., intravenously) to a human subject, a compound of the disclosure can be dosed at a rate of from about 5 μg/kg/min to about 100 μg/kg/min. In certain embodiments, a compound of the disclosure can be dosed to a human subject at a rate of from about 10 μg/kg/min to about 70 μg/kg/min. In certain embodiments, a compound of the disclosure can be dosed to a human subject at a rate of from about 15 μg/kg/min to about 50 μg/kg/min. In certain embodiments, a compound of the disclosure can be dosed to a human subject at a rate of from about 20 μg/kg/min to about 40 μg/kg/min.

In another embodiment, the compounds of the disclosure can be formulated for oral administration. Compounds for oral administration can be formulated as liquid or solid dosage forms. In particular embodiments where a nitroxyl donating compound is formulated as an oral liquid dosage form, polyethylene glycol 300 (PEG300) can serve as an exemplary excipient.

3. BRIEF DESCRIPTION OF FIGURES

FIG. 1 shows the hemodynamic profile of CXL-1020 and two compounds of the disclosure (compounds of formula (1) and formula (2)) using a tachycardia-pacing model of heart failure (see Example 6). Each compound was administered intravenously at a rate of 100 μg/kg/min. Hemodynamic parameters were obtained 180 minutes after administration of the respective compound.

FIG. 2 shows the hemodynamic profile of the compound of formula (1) at various dosages using a tachycardia-pacing model of heart failure for conscious animals (see Example 6).

FIG. 3 shows the hemodynamic profile of the compound of formula (1) following induction of heart failure in dogs. Hemodynamics were evaluating using a canine microembolization heart failure model (see Example 7). The data is shown for final time point during infusion (180 minutes) at two rates of infusion.

4. DETAILED DESCRIPTION

Figure 1:
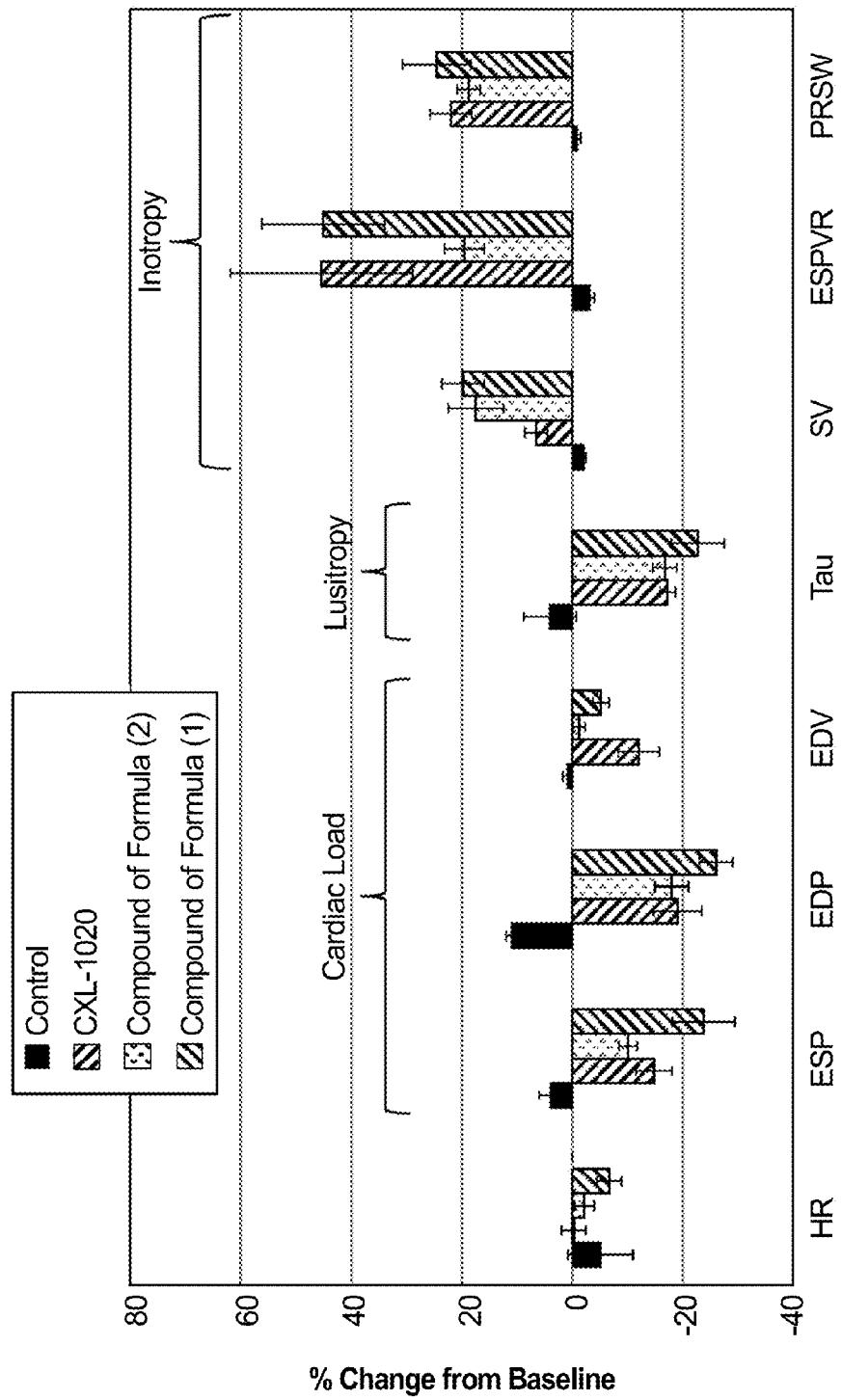

The invention includes the following:
(1.) A compound of formula (1):

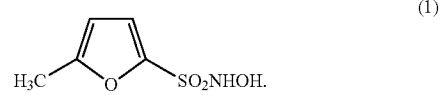

(2.) A compound of formula (2):

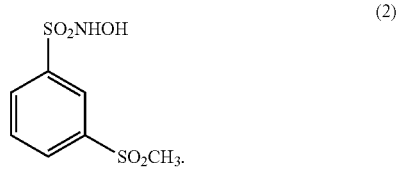

(3.) A pharmaceutical composition comprising a compound of the above (1.) or the above (2.) and at least one pharmaceutically acceptable excipient.

(4.) The pharmaceutical composition of the above (3.), wherein the pharmaceutical composition is suitable for intravenous administration.

(5.) The pharmaceutical composition of the above (3.) or the above (4.), wherein the pharmaceutical composition has a pH of from about 4 to about 6.

(6.) The pharmaceutical composition of any one of the above (3.)-(5.), wherein the pharmaceutical composition has a pH of from about 4 to about 5.

(7.) The pharmaceutical composition of any one of the above (3.)-(6.), wherein the pharmaceutical composition has a pH of about 4.

(8.) A method of treating a cardiovascular disease, comprising administering an effective amount of compound of the above (1.) or the above (2.) or the pharmaceutical composition of any one of the above (3.)-(7.) to a patient in need thereof.

(9.) The method of the above (8.), wherein the cardiovascular disease is heart failure.

(10.) The method of the above (8.) or the above (9.), wherein the cardiovascular disease is acute decompensated heart failure.

(11.) The method of any one of the above (8.)-(10.), wherein the compound or pharmaceutical composition is administered intravenously.

(12.) The method of any one of the above (8.)-(11.), wherein the compound or pharmaceutical composition is administered at a dose of from about 20 μg compound of formula (1) or (2)/kg/minute to about 40 μg compound of formula (1) or (2)/kg/minute.

(13.) The method of any one of the above (8.)-(10.), wherein the compound or pharmaceutical composition is administered orally.

(14.) A kit comprising a compound of the above (1.) or the above (2.) in dry form or the pharmaceutical composition of any one of the above (3.)-(7.) in dry form; and
a pharmaceutically acceptable liquid diluent.

(15.) Use of the compound of the above (1.) or the above (2.) or use of the pharmaceutical composition of any one of the above (3.)-(7.) for the manufacture of a medicament useful for treating a cardiovascular disease.

(16.) Use of the compound of the above (1.) or the above (2.) or use of the pharmaceutical composition of any one of the above (3.)-(7.) for the manufacture of a medicament useful for treating heart failure.

(17.) Use of the compound of the above (1.) or the above (2.) or use of the pharmaceutical composition of any one of the above (3.)-(7.) for the manufacture of a medicament useful for treating acute decompensated heart failure.

(18.) The compound of the above (1.) or the above (2.) or the pharmaceutical composition of any one of the above (3.)-(7.) for use in the treatment of a cardiovascular disease.

(19.) The compound of the above (1.) or the above (2.) or the pharmaceutical composition of any one of the above (3.)-(7.) for use in the treatment of heart failure.

(20.) The compound of the above (1.) or the above (2.) or the pharmaceutical composition of any one of the above (3.)-(7.) for use in the treatment of acute decompensated heart failure.

4.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl)amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20<sup>th</sup> Ed. (Lippincott Williams & Wilkins, Baltimore, Md., 2000) and *Handbook of Pharmaceutical Excipients*, American Pharmaceutical Association, Washington, D.C., (e.g., 1<sup>st</sup>, 2<sup>nd</sup> and 3<sup>rd</sup> Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to, a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg. Badesch et al., *J. Amer. Coll. Cardiol.* 54(Suppl.):S55-S66 (2009).

"N/A" means not assessed.

"$(C_1$-$C_6)$alkyl" refers to saturated linear and branched hydrocarbon structures having 1, 2, 3, 4, 5 or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1$-$C_6)$ alkyl groups include methyl, ethyl, n-propyl, iso-propyl, n-butyl, tert-butyl, n-hexyl, and the like.

"$(C_1$-$C_4)$alkyl" refers to saturated linear and branched hydrocarbon structures having 1, 2, 3, or 4 carbon atoms. Examples of $(C_1$-$C_4)$alkyl groups include methyl, ethyl, n-propyl, iso-propyl, n-butyl and tert-butyl.

"$(C_3$-$C_5)$alkyl" refers to saturated linear and branched hydrocarbon structures having 3, 4, or 5 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_3$-$C_5)$ alkyl groups include n-propyl, iso-propyl, n-butyl, tert-butyl, n-pentyl, and the like.

"$(C_2$-$C_4)$alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"$(C_2$-$C_3)$alkynyl" refers to a straight chain non-cyclic hydrocarbon having 2 or 3 carbon atoms and including at least one carbon-carbon double bond. Examples of $(C_2$-$C_3)$alkenyls include -vinyl, -allyl, and 1-prop-1-enyl.

"$(C_5$-$C_7)$heterocycloalkyl" refers to a 5-, 6-, or 7-membered, saturated or unsaturated, bridged, mono- or bicyclic-heterocycle containing 1, 2, 3, or 4 ring heteroatoms each independently selected from nitrogen, oxygen, and sulfur. Examples of $(C_5$-$C_7)$heterocycloalkyl groups include pyrazolyl, pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrazole, piperidine, pyridazine, pyrimidine, pyrazine, tetrahydrofuranone, γ-butyrolactone, α-pyran, γ-pyran, dioxolane, tetrahydropyran, dioxane, dihydrothiophene, piperazine, triazine, tetrazine, morpholine, thiomorpholine, diazepan, oxazine, tetrahydro-oxazinyl, isothiazole, pyrazolidine, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. Examples of -(5- or 6-membered)heteroaryls include pyridyl, pyrrolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"Halo" refers to —F, —Cl, —Br or —I.

"Sulfo-n-butyl ether derivative of β-cyclodextrin" refers to β-cyclodextrin having at least one —OH group that is derivatized by replacing the hydrogen atom thereof with —(CH$_2$)$_4$—S(O)$_2$—OH or —(CH$_2$)$_4$—S(O)$_2$—O$^-$Z$^+$ to provide a —O—(CH$_2$)$_4$—S(O)$_2$—OH or —O—(CH$_2$)$_4$—S(O)$_2$—O$^-$Z$^+$ group, respectively, where Z$^+$ is a cation such as sodium, potassium, ammonium, tetramethylammonium, and the like. In one embodiment, each Z is sodium.

4.2 Nitroxyl Donating Compounds with Improved Therapeutic Index

In one aspect, the disclosure provides novel compounds suitable for treating cardiovascular diseases (e.g., heart failure). In particular, the disclosure provides nitroxyl donating compounds that have a combination of properties that make them suitable for use as a human therapeutic. In particular, the nitroxyl donating compounds of the disclosure have suitable half-lives, a favorable therapeutic index, are highly water soluble and have sufficient solid state stability. Table 1 provides two specific N-hydroxysulfonamide nitroxyl donating compounds of the disclosure that possess such desirable properties and are thus suitable for therapeutic administration to humans.

TABLE 1

Nitroxyl Donating Compounds of the Disclosure

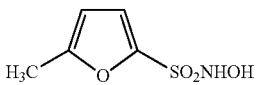

N-Hydroxy-5-methylfuran-2-sulfonamide

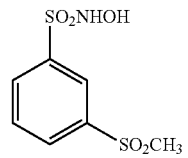

N-Hydroxy-3-methanesulfonylbenzene-1-sulfonamide

In particular embodiments, the nitroxyl donating compounds in Table 1 can be utilized as a pharmaceutically acceptable salt thereof.

In other embodiments, the N-hydroxy group of the compounds listed in Table 1 can be esterified to provide prodrugs of the compounds.

For instance, the disclosure provides compounds of the formula (3):

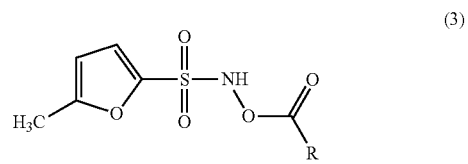

wherein R is hydrogen, —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH$_2$, —NH—(C$_1$-C$_4$)alkyl, or —N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with one or more substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(=O)(C$_1$-C$_4$)alkyl, —C(=O)O(C$_1$-C$_4$)alkyl, —OC(=O)(C$_1$-C$_4$)alkyl, —OC(=O)NH$_2$, —S(=O)(C$_1$-C$_4$)alkyl, or —S(=O)$_2$(C$_1$-C$_4$)alkyl. In particular embodiments, R is methyl, ethyl, benzyl, or phenyl.

In particular embodiments where the compound of the disclosure is a compound of the formula (3), R is methyl. In other embodiments where the compound has the formula (3), R is ethyl. In certain embodiments where the compound of the disclosure is a compound of the formula (3), R is methyl or ethyl. In other embodiments where the compound where the compound has the formula (3), R is phenyl. In other embodiments where the compound has the formula (3), R is benzyl. In particular embodiments where the compound of the disclosure is a compound of the formula (3), R is benzyl or phenyl. In other embodiments where the compound has the formula (3), R is —NH$_2$. In each of the above embodiments in this paragraph, R is unsubstituted in one embodiment, monosubstituted in another embodiment, di-substituted with two independently selected substituents in an additional embodiment, or tri-substituted with three independently selected substituents in a further embodiment. In various embodiments of each of the above embodiments in this paragraph, the substituent is -halo, —NH$_2$, —NHCH$_3$, —CF$_3$, or —OCH$_3$ or the substituents are independently selected from -halo, —NH$_2$, —NHCH$_3$, —CF$_3$, and —OCH$_3$.

For instance, the disclosure provides compounds of the formula (4):

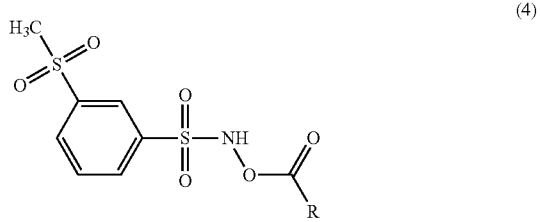

wherein R and its optional substituent(s) are as defined above with respect to the compound of formula (3).

In particular embodiments where the compound of the disclosure is a compound of the formula (4), R is methyl. In other embodiments where the compound has the formula (4), R is ethyl. In certain embodiments where the compound of the disclosure is a compound of the formula (4), R is methyl or ethyl. In other embodiments where the compound where the compound has the formula (4), R is phenyl. In other embodiments where the compound has the formula (4), R is benzyl. In particular embodiments where the compound of the disclosure is a compound of the formula (4), R is benzyl or phenyl. In other embodiments where the compound has the formula (4), R is —$NH_2$. In each of the above embodiments in this paragraph, R is unsubstituted in one embodiment, mono-substituted in another embodiment, di-substituted with two independently selected substituents in an additional embodiment, or tri-substituted with three independently selected substituents in a further embodiment. In various embodiments of each of the above embodiments in this paragraph, the substituent is -halo, —$NH_2$, —$NHCH_3$, —$CF_3$, or —$OCH_3$ or the substituents are independently selected from -halo, —$NH_2$, —$NHCH_3$, —$CF_3$, and —$OCH_3$.

Unexpectedly, it has been discovered that the nitroxyl donating compounds of the disclosure provide levels of efficacy similar to CXL-1020 when administered to human patients, but with significantly reduced side effects, notably local side effects (e.g., irritation and/or inflammation) (see Examples 8 and 9). Moreover, nitroxyl donating compounds of the disclosure provide an onset of hemodynamic effects in 1 hour or less, which is desirable from a clinical perspective.

Without being bound by theory, the experiments reported in the Examples of this disclosure suggest that nitroxyl donors with half-lives substantially shorter than 15 minutes when measured in PBS or human plasma (see Example 4), such as CXL-1020, produce high local concentrations of nitroxyl upon administration, and that the high local concentration of nitroxyl is a cause of the observed undesirable side effects. Nitroxyl at high concentration is known to dimerize, resulting in the formation of hyponitrous acid, which is capable of producing hydroxyl radicals. Alternatively, or in addition, peroxide emanating from white blood cells can react with nitroxyl to form hydroxyl radicals. Hydroxyl radicals can be toxic to endothelial cells, resulting in inflammation and/or intolerance. While nitroxyl compounds with longer half-lives could, in theory, produce hydroxyl radicals through similar mechanisms, formation of such radicals would be expected to be reduced by virtue of the low concentrations of nitroxyl, thus reducing the ability of nitroxyl to dimerize or to react with peroxide. Compounds with very long half-lives (e.g., greater than 95 minutes when measured in human plasma in accordance with the method described in Example 4) would therefore be expected to have a favorable toxicological profile; however, because these compounds would be expected to be cleared from the circulation and/or diluted prior to substantial nitroxyl formation, such compounds are expected to have low efficacy.

As described in Example 4, compounds of formulas (1) and (2) have half-lives greater than about 10 minutes and less than 95 minutes when measured in an aerated phosphate buffered saline (PBS) solution at a pH of 7.4, and when measured in human plasma at pH 7.4 in the presence of an anticoagulant (e.g., heparin or sodium citrate), each measured under conditions specified in Example 4. In particular, the compound of formula (1) has a half-life of approximately 68 minutes when measured in an aerated phosphate buffered saline (PBS) solution at a pH of 7.4, and approximately 65 minutes when measured in human plasma at pH 7.4 in the presence of an anticoagulant (e.g., heparin or sodium citrate), each measured under conditions specified in Example 4. The compound of formula (2) has a half-life of approximately 50 minutes when measured in an aerated phosphate buffered saline (PBS) solution at a pH of 7.4, and approximately 37 minutes when measured in human plasma at pH 7.4 in the presence of an anticoagulant (e.g., heparin or sodium citrate), each measured under conditions specified in Example 4.

Furthermore, as described in Example 5, each of the compounds of formulas (1) and (2) is highly water soluble and is thus amenable to parenteral or oral administration. The compounds can be formulated without the addition of a solubilizing agent. Moreover, as demonstrated in Examples 10-12, the compounds of formula (1) and formula (2) have excellent stability in pharmaceutical compositions for parenteral (e.g., intravenous) administration.

4.3 Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline (PBS) or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a nitroxyl donor of the disclosure compound herein donates from about 70% to about 90% of its theoretical maximum amount of nitroxyl. In particular embodiments, a nitroxyl donor of the disclosure compound herein donates from about 85% to about 95% of its theoretical maximum amount of nitroxyl. In particular embodiments, a nitroxyl donor of the disclosure compound herein donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

If desired, nitroxyl donation also can be detected by exposing the test compound to metmyoglobin ($Mb^{3+}$). See Bazylinski et al., *J. Amer. Chem. Soc.* 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance (EPR). The $Mb^{2+}$—NO complex has an EPR signal centered around a g-value of about 2. Nitric oxide, on the other hand, reacts with $Mb^{3+}$ to form an $Mb^{3+}$—NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

Testing for nitroxyl donation can be performed at a physiologically relevant pH. The nitroxyl donating compounds of the disclosure are capable of donating nitroxyl at physiological pH (i.e., a pH of about 7.4) and physiological temperature (i.e., a temperature of about 37° C.) (together, "physiological conditions"). In particular embodiments, a nitroxyl donating compound of the disclosure can donate about 40% or more of its theoretical maximum (i.e., 100%) amount of nitroxyl under physiological conditions. In particular embodiments, a nitroxyl donating compound of the disclosure can donate about 50% or more of its theoretical maximum amount of nitroxyl under physiological conditions. In particular embodiments, a nitroxyl donating compound of the disclosure can donate about 60% or more of its theoretical maximum amount of nitroxyl under physiological conditions. In particular embodiments, a nitroxyl donating compound of the disclosure can donate about 70% or more of its theoretical maximum amount of nitroxyl under physiological conditions. In particular embodiments, a nitroxyl donating compound of the disclosure can donate about 80% or more of its theoretical maximum amount of nitroxyl under physiological conditions. In particular embodiments, a nitroxyl donating compound of the disclosure can donate about 90% or more of its theoretical maximum amount of nitroxyl under physiological conditions.

It will be understood that a nitroxyl donating compound of the disclosure might also donate a limited amount of nitric oxide, so long as the amount of nitroxyl donation exceeds the amount of nitric oxide donation. In certain embodiments, a nitroxyl donating compound can donate about 25 mole % or less of nitric oxide under physiological conditions. In particular embodiments, a nitroxyl donating compound can donate about 20 mole % or less of nitric oxide under physiological conditions. In particular embodiments, a nitroxyl donating compound can donate about 15 mole % or less of nitric oxide under physiological conditions. In particular embodiments, a nitroxyl donating compound can donate about 10 mole % or less of nitric oxide under physiological conditions. In particular embodiments, a nitroxyl donating compound can donates about 5 mole % or less of nitric oxide under physiological conditions. In particular embodiments, a nitroxyl donating compound can donate about 2 mole % or less of nitric oxide under physiological conditions. In particular embodiments, a nitroxyl donating compound can donate an insignificant amount (e.g., about 1 mole % or less) of nitric oxide under physiological conditions.

4.4 Pharmaceutical Compositions

The disclosure also encompasses pharmaceutical compositions comprising a nitroxyl donating compound of formulae (1), (2), (3), or (4) and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

In various embodiments, the at least one pharmaceutically acceptable excipient comprises at least one species of cyclodextrin. In a particular embodiment, the cyclodextrin is a cyclic structure having glucose units linked by $\alpha$(1-4) linkages. In another embodiment, the cyclodextrin is a $\beta$-cyclodextrin, i.e., a cyclic structure having seven glucose units linked by $\alpha$(1-4) linkages. In another embodiment, the cyclodextrin is chemically modified by derivatizing any combination of the three available hydroxyl groups on each glucopyranose unit thereof.

In some embodiments where the pharmaceutically acceptable excipient comprises at least one species of cyclodextrin, the cyclodextrin is a sulfo($C_1$-$C_6$)alkyl ether derivative of $\beta$-cyclodextrin. In certain of these embodiments, the cyclodextrin is a sulfo($C_1$-$C_6$)alkyl ether derivative of $\beta$-cyclodextrin having from about six to about seven sulfo($C_1$-$C_6$)alkyl ether groups per cyclodextrin molecule. In various embodiments, the cyclodextrin is a sulfo($C_1$-$C_6$)alkyl ether derivative of $\beta$-cyclodextrin having an average of from about six to about seven sulfo($C_1$-$C_6$)alkyl ether groups per cyclodextrin molecule. In another such embodiment, the cyclodextrin is a sulfo($C_1$-$C_6$)alkyl ether derivative of $\beta$-cyclodextrin having six or seven sulfo($C_1$-$C_6$)alkyl ether groups per cyclodextrin molecule.

In a particular series of embodiments where the pharmaceutically acceptable excipient comprises at least one species of cyclodextrin, the cyclodextrin is a sulfo($C_3$-$C_5$)alkyl ether derivative of $\beta$-cyclodextrin. In one such embodiment, the cyclodextrin is a sulfo($C_3$-$C_5$)alkyl ether derivative of $\beta$-cyclodextrin having from about six to about seven sulfo($C_3$-$C_5$) alkyl ether groups per cyclodextrin molecule. In various such embodiments, the cyclodextrin is a sulfo($C_3$-$C_5$)alkyl ether derivative of $\beta$-cyclodextrin having an average of from about six to about seven sulfo($C_3$-$C_5$)alkyl ether groups per cyclodextrin molecule. In another such embodiment, the cyclodextrin is a sulfo($C_3$-$C_5$)alkyl ether derivative of $\beta$-cyclodextrin having six or seven sulfo($C_3$-$C_5$)alkyl ether groups per cyclodextrin molecule.

In particular embodiments where the pharmaceutically acceptable excipient comprises at least one species of cyclodextrin, the cyclodextrin is a sulfobutyl ether derivative of $\beta$-cyclodextrin. In certain of these embodiments, the cyclodextrin is a sulfobutyl ether derivative of $\beta$-cyclodextrin having from about six to about seven sulfobutyl ether groups per cyclodextrin molecule. In another such embodiment, the cyclodextrin is a sulfobutyl ether derivative of $\beta$-cyclodextrin having an average of from about six to about seven sulfobutyl ether groups per cyclodextrin molecule. In another such embodiment, the cyclodextrin is a sulfobutyl ether derivative of $\beta$-cyclodextrin having six or seven sulfobutyl ether groups per cyclodextrin molecule.

In certain embodiments where the pharmaceutically acceptable excipient comprises at least one species of cyclodextrin, the cyclodextrin is a sulfo-n-butyl ether derivative of $\beta$-cyclodextrin. In one such embodiment, the cyclodextrin is a sulfo-n-butyl ether derivative of $\beta$-cyclodextrin having from about six to about seven sulfo-n-butyl ether groups per cyclodextrin molecule. In another such embodiment, the cyclodextrin is a sulfo-n-butyl ether derivative of $\beta$-cyclodextrin having an average of from about six to about seven sulfo-n-butyl ether groups per cyclodextrin molecule. In another such embodiment, the cyclodextrin is a sulfo-n-butyl ether derivative of $\beta$-cyclodextrin having six or seven sulfo-n-butyl ether groups per cyclodextrin molecule.

In various particular embodiments where the pharmaceutically acceptable excipient comprises at least one species of cyclodextrin, the cyclodextrin comprises a plurality of negative charges at physiologically compatible pH values, e.g., at a pH of from about 5.0 to about 6.8 in some embodiments, from about 5.5 to about 6.5 in some embodiments, from about 5.7 to about 6.3 in some embodiments, from about 5.8 to about 6.2 in some embodiments, from about 5.9 to about 6.1 in some embodiments, and about 6.0 in particular embodiments. In one such embodiment, the at least one pharmaceutically acceptable excipient comprises CAPTISOL® cyclodextrin (Ligand Pharmaceuticals, La Jolla, Calif.).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. Compounds for oral administration can be formulated as liquid or solid dosage forms. In particular embodiments where the nitroxyl donating compounds are formulated as oral liquid dosage forms, polyethylene glycol 300 (PEG300) can usefully serve as an excipient.

The compounds and pharmaceutical compositions disclosed herein can be prepared as any appropriate unit dosage form, such as capsules, sachets, tablets, powder, granules, solution, suspension in an aqueous liquid, suspension in a non-aqueous liquid, oil-in-water liquid emulsion, water-in-oil liquid emulsion, liposomes or bolus.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions comprising a nitroxyl donating compound of the disclosure can be formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the nitroxyl donating compounds in less acidic or even neutral solutions (see FIG. 4). Accordingly, in particular embodiments, a nitroxyl donating compounds of the disclosure can be formulated for parenteral use at a pH of from about 5 to about 6.2 (e.g., pH of about 5, about 5.5, about 5.8, about 6, or about 6.2, including values there between).

4.5 Methods of Using the Compounds and Pharmaceutical Compositions of the Disclosure In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension (PH).

4.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

4.5.1.1 Heart Failure

The nitroxyl donating compounds and compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure (CHF) and acute congestive heart failure. In one embodiment, the compounds and compositions of the disclosure can be used to treat acute decompensated heart failure.

In embodiments where the nitroxyl donating compounds and compositions of the disclosure are used to treat patients suffering from heart failure, another active agent that treats heart failure can also be administered. In one such embodiment, the nitroxyl donor can be administered in conjunction with a positive inotrope such as a beta-agonist. Examples of beta-agonists include, without limitation, dopamine, dobutamine, isoproterenol, analogs of such compounds and derivatives of such compounds. In another embodiment, nitroxyl donor can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Figure 2:
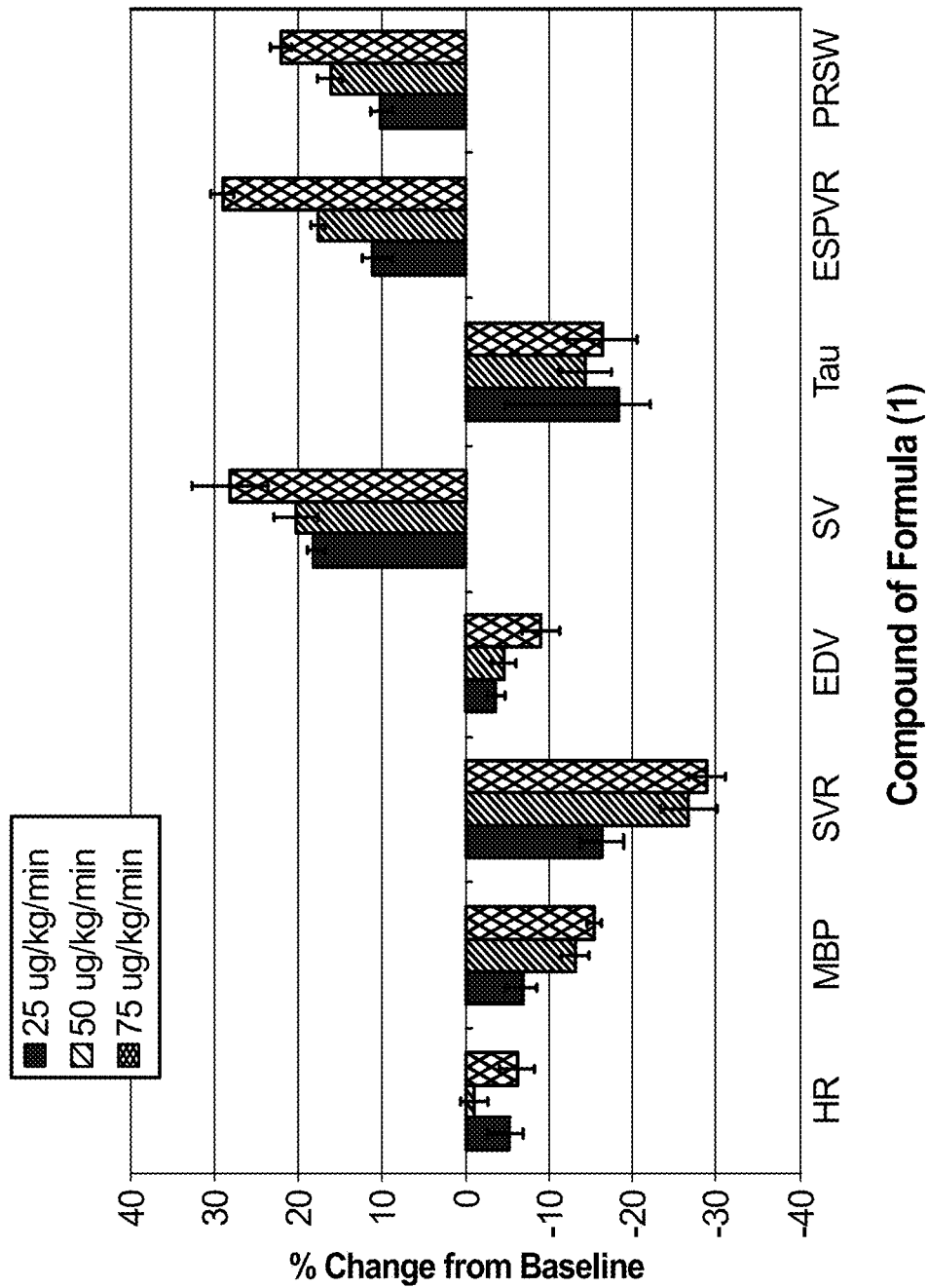
Figure 3:
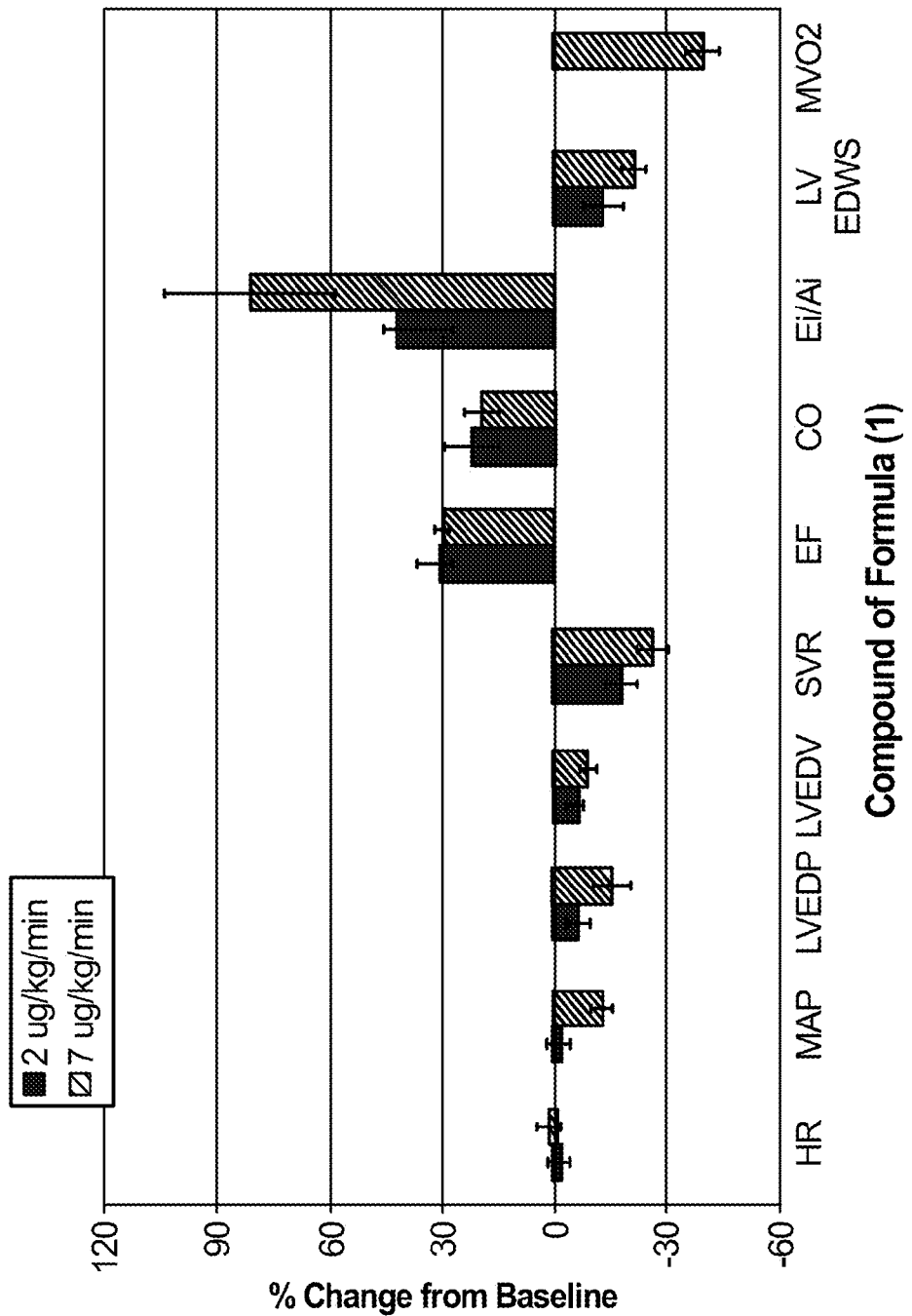

As described in Examples 6 and 7, various heart failure models were used to evaluate the hemodynamic profiles of several of the nitroxyl donating compounds of the disclosure. As shown in FIGS. 1-3, which are discussed in Examples 6 and 7, the compounds of formula (1) and formula (2) produced, for example, significant enhancement of inotropy and lusitropy, and modest reductions in blood pressure without tachycardia. Moreover, the onset of significant hemodynamic effects was rapid (e.g., within 1 hour) and for near-maximal effect was achieved within 2 hours.

Figure 4:
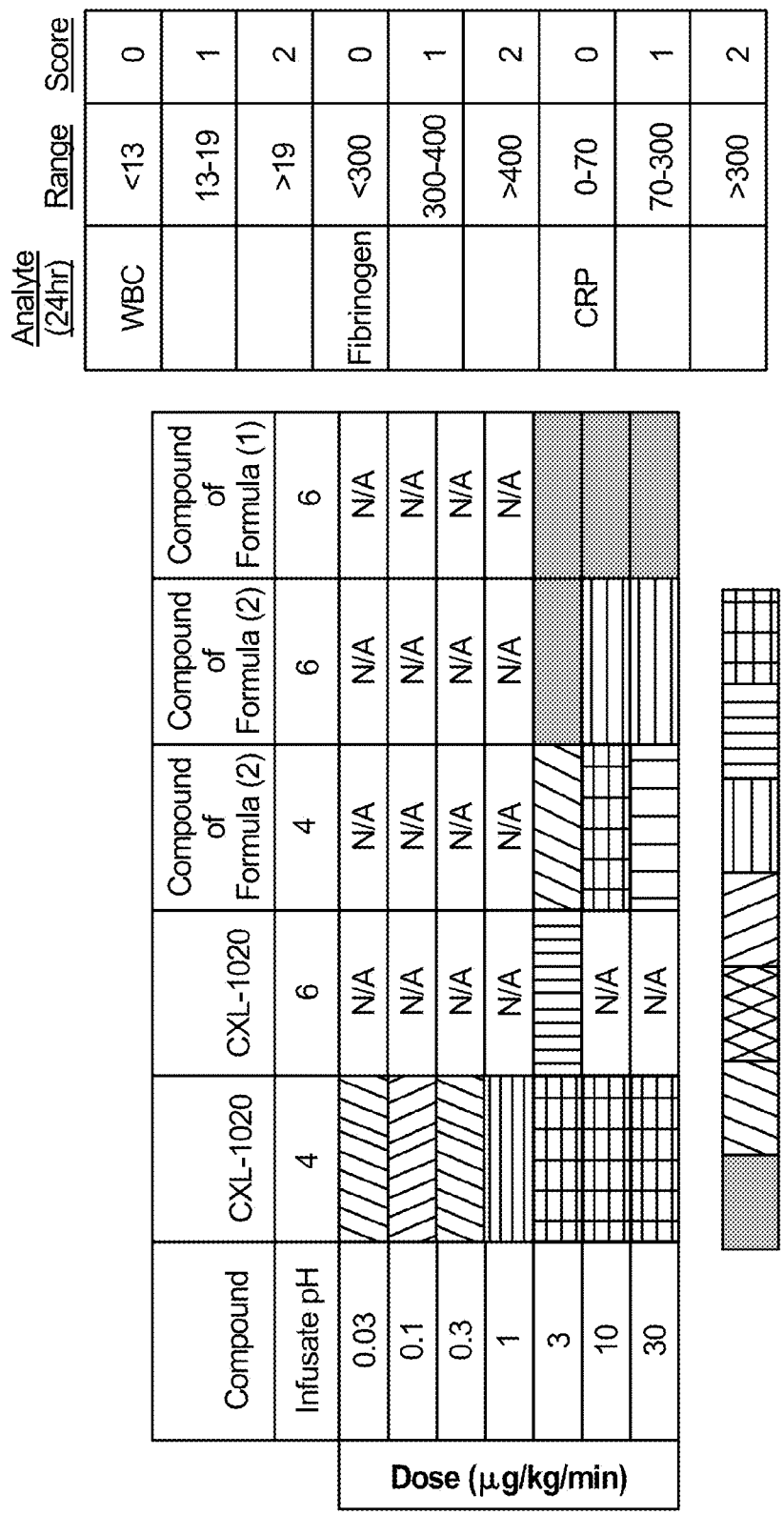
FIG. 4 shows the assessment of the toxicological profile of CXL-1020 and two nitroxyl donating compounds of the disclosure (compounds of formula (1) and formula (2)) following 24 hour infusion at different doses using a canine peripheral vein model (see Example 9). Key inflammatory markers measured include white blood cells (WBC), fibrinogen, and C-reactive protein (CRP).
Figure 5:
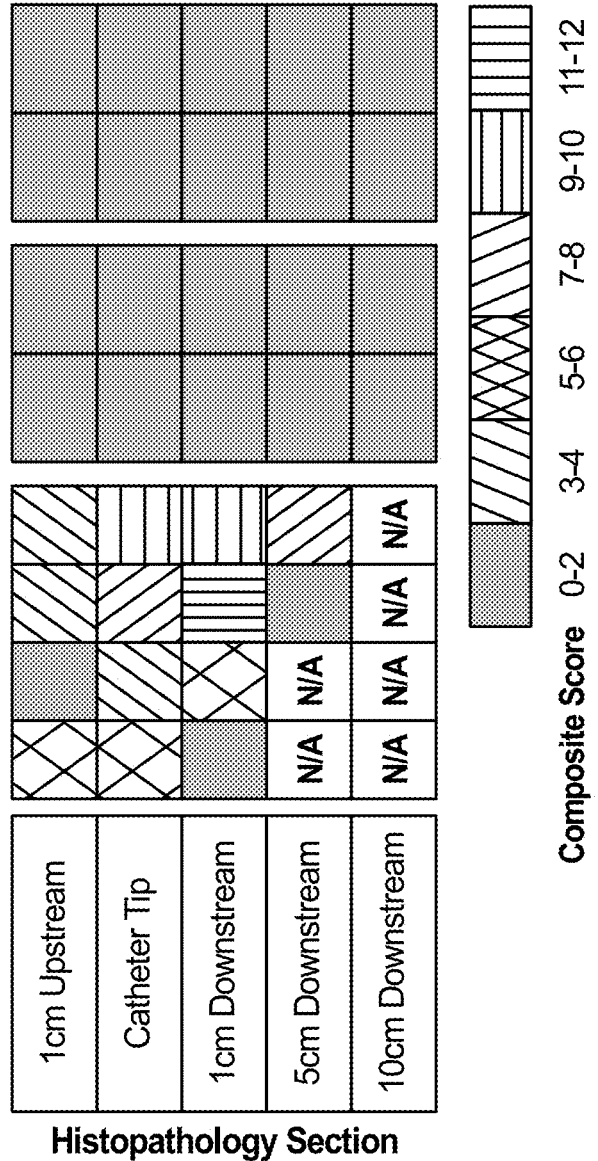
FIG. 5 shows measures of inflammation observed using a canine implanted central catheter 72 hour model using different doses of CXL-1020 and the compounds of formula (1) and (2) (see Example 9).

While the hemodynamic activity of compounds of formula (1) and formula (2) are similar to compositions comprising the nitroxyl donor CXL-1020 when administered intravenously, the toxicological profile of compounds of formula (1) and formula (2), which have longer half-lives than CXL-1020, is significantly improved as compared to compositions comprising CXL-1020 (see Example 9 and FIGS. 4 and 5). For example, the "No Observed Adverse Effect Levels" (NOAEL) of the compounds of formula (1) and formula (2) were substantially higher than the NOAEL for CXL-1020 (see Example 9 for description of NOAEL determination). In particular, the compound of formula (1) has the most favorable toxicological profile of all N-hydroxysulfonamide type nitroxyl donors tested thus far and shows no adverse effects on clinical markers of inflammation when administered intravenously at concentrations at least as high as 30 μg/kg/min (FIG. 4). In contrast, CXL-1020 begins to show undesirable side effects at concentrations as low as 0.3 μg/kg/min.

4.5.1.2 Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident (CVA).

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3):625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

4.5.2 Pulmonary Hypertension

In another embodiment, a compounds or pharmaceutical composition of the disclosure can be used to prevent or delay the onset and/or development of pulmonary hypertension. In one such embodiment, a compounds or pharmaceutical composition of the disclosure can be used to prevent or delay the onset and/or development of pulmonary arterial hypertension (PAH).

In another embodiment, the disclosed subject matter provides a method of reducing mean pulmonary arterial pressure (MPAP), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

4.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the present disclosure is administered, dosages are expressed based on the amount of active pharmaceutical ingredient, i.e., the amount of nitroxyl donor compound(s) of the disclosure present in the pharmaceutical composition.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the compound or pharmaceutical composition of the present disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min In some embodiments, the compound or pharmaceutical composition of the present disclosure is administered intravenously in an amount ranging from about 0.1 µg/kg/min to about 100 µg/kg/min, about 1 µg/kg/min to about 100 µg/kg/ min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the compound or pharmaceutical composition of the present disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a compound or pharmaceutical composition of the present disclosure is administered intravenously in an amount of from about 20 µg/kg/min to about 30 µg/kg/min.

In a variety of embodiments, including various oral administration embodiments, the compounds or pharmaceutical compositions of the disclosure are administered according to a weight-based daily dosing regimen, either as a single daily dose (QD) or in multiple divided doses administered, e.g., twice a day (BID), three times a day (TID), or four times a day (QID).

In certain embodiments, the nitroxyl donating compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the nitroxyl donating compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the compound or pharmaceutical composition of the disclosure is administered in a dose range of about 3 to about 30 mg/kg, administered from once a day (QD) to three times a day (TID).

In certain embodiments, compounds or pharmaceutical compositions of the disclosure are administered according to a flat (i.e., non-weight-based) dosing regimen, either as a single daily dose (QD) or in multiple divided doses administered, e.g., twice a day (BID), three times a day (TID), or four times a day (QID).

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

4.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

5. EXAMPLES

The following examples are presented for illustrative purposes and should not serve to limit the scope of the disclosed subject matter.

5.1 Synthesis of Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

Example 1

Preparation of N-Hydroxy-5-methylfuran-2-sulfonamide (1)

To a solution of hydroxylamine (0.92 mL of a 50% aqueous solution; 13.8 mmol) in THF (6 mL) and water (2 mL) cooled to 0° C. was added 5-methylfuran-2-sulfonyl chloride (1 g, 5.5 mmol) as a solution in THF (6 mL) dropwise so as to maintain the temperature below 10° C. The reaction was stirred for 5 minutes, after which time TLC (1:1 hexane:ethyl acetate (H:EA)) showed substantially complete consumption of the sulfonyl chloride. The reaction was diluted twice with 50 mL dichloromethane (DCM) and the organic portion was separated and washed with water (10 mL). The organic portion was dried over sodium sulfate, filtered and concentrated under reduced pressure. The product was chromatographed by silica gel chromatography eluting with heptanes:EtOAc followed by trituration with heptane to provide the title compound as a yellow solid (0.59 g, yield 61%). LC-MS $t_R$=0.91 min; $^1$H NMR (DMSO, 500 MHz) δ ppm 9.82 (1H, d, J=3.1 Hz), 9.64 (1H, d, J=3.2 Hz), 7.10 (1H, d, J=3.4 Hz), 6.36 (1H, d, J=3.4 Hz), 2.36 (3H, s).

Example 2

Preparation of N-Hydroxy-3-methanesulfonylbenzene-1-sulfonamide (2)

3-Methanesulfonylbenzene-1-sulfonyl chloride

The intermediate 3-methanesulfonylbenzene-1-sulfonyl chloride was synthesized according to the methods disclosed in Park et al., *J. Med. Chem.* 51(21):6902-6915 (2008). Specifically, methyl sulfonyl benzene (110 g, 0.7 mol) was heated for 18 hours at 90° C. in chlorosulfonic acid (450 mL, 6.7 mol) after which time the reaction mixture was allowed to cool to a temperature of about 21° C. before slowly being poured onto crushed ice. The resulting slurry was twice extracted into EtOAc (2 L for each extraction). The organic portions were combined and washed with brine (50 mL) before being dried over sodium sulfate, filtered and concentrated under reduced pressure to provide the intermediate sulfonyl chloride as an off white solid (125 g, yield 75%). $^1$H NMR (400 MHz, CDCl$_3$) δ ppm 8.61 (1 h, t, J=1.7 Hz), 8.35-8.31 (2H, m), 7.90 (1H, t, J=7.9 Hz), 3.15 (3H, s).

N-Hydroxy-3-methanesulfonylbenzene-1-sulfonamide

To a solution of aqueous hydroxylamine (16 mL of a 50% aqueous solution, 245 mmol) in THF (150 mL) and water (25 mL) cooled to −5° C. was slowly added 3-methanesulfonylbenzene-1-sulfonyl chloride (25 g, 98 mmol) while maintaining a reaction temperature of less than 10° C. The reaction was maintained at this temperature until substantially complete consumption of the sulfonyl chloride was observed (about 5 min), after which time the reaction was diluted with DCM (250 mL), the organic portion was separated and washed twice with 50 mL of water. The aqueous extracts were combined and rewashed twice with DCM (250 mL for each wash). All of the organic portions were combined, dried over sodium sulfate, filtered and concentrated under reduced pressure to provide the title compound as a beige solid. Trituration was carried out using heptanes:EtOAc (1:1; v:v) to provide the title compound as a beige solid (14 g, yield 56%). LC-MS $t_R$=0.90 min; High Resolution Mass Spectroscopy (HRMS): theoretical ($C_7H_9NO_5S_2$)=249.9844, measured=249.9833; $^1$H NMR (500 MHz, DMSO-$d_6$) δ ppm 9.85 (2H, q, J=3.3 Hz), 8.31 (1H, t, J=1.6 Hz), 8.28 (1H, dt, J=7.8, 1.3 Hz), 8.14-8.19 (1H, m), 7.93 (1H, t, J=7.9 Hz), 3.32 (3H, s).

5.2 Example 3

Nitroxyl Production as Determined via $N_2O$ Quantification

Nitrous oxide ($N_2O$) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce $N_2O$ (see Mincione et al., *J. Enzyme Inhibition* 13:267-284 (1998); and Scozzafava et al., *J. Med. Chem.* 43:3677-3687 (2000)). Using either nitrous oxide gas or Angeli's salt (AS) as a standard, the relative amounts of $N_2O$ released from compounds of the disclosure was examined via gas chromatography (GC) headspace analysis.

A procedure for determining the relative amounts of $N_2O$ released from compounds of the disclosure is as follows. GC was performed on an Agilent gas chromatograph equipped with a split injector (10:1 splitting), microelectron capture detector, and a HP-MOLSIV 30 m×0.32 mm×25 μm molecular sieve capillary column. Helium was used as the carrier (4 mL/min) gas and nitrogen was used as the make-up (20 mL/min) gas. The injector oven and the detector oven were kept at 200° C. and 325° C., respectively. All nitrous oxide analyses were performed with the column oven held at a constant temperature of 200° C.

All gas injections were made using an automated headspace analyzer. Vial pressurization was 15 psi. The analyzer's sample oven, sampling valve, and transfer line were kept at 40° C., 45° C., and 50° C., respectively. The oven stabilization, vial pressurization, loop fill, loop equilibration, and sample injection times were 1.00 min., 0.20 min., 0.20 min., 0.05 min., and 1.00 min., respectively.

All determinations used a batch of nominal 20 mL headspace vials with volumes pre-measured for sample uniformity (actual vial volume varied by <2.0% relative standard deviation (n=6)). The average vial volume for the batch was determined from six randomly-selected vials by calculating the weight difference between the capped and sealed empty (i.e., air-filled) vial and the capped and sealed deionized water-filled vial using the known density of deionized water, then averaging. Blanks were prepared by sealing and capping two vials then purging each for 20 seconds with a gentle argon stream. Nitroxyl standards were prepared by sealing and capping four vials then purging each for 1 minute with a gentle stream, from a gas cylinder, of a 3000 ppm nitroxyl standard.

CXL-1020 (N-hydroxy-2-methanesulfonylbenzene-1-sulfonamide) "standards" were prepared by, in duplicate, accurately weighing 10±0.5 mg of CXL-1020 and adding it to each 4 mL vial. Using an auto pipette, 1 mL of argon-purged anhydrous DMF (Sigma-Aldrich) was added to each 4 mL vial to form a CXL-1020 stock solution for each sample and the vials were capped and shaken and/or sonicated to insure complete dissolution upon visual observation. Using an auto pipette, 20 mL vials were charged with 5 mL of PBS (purged for at least 30 min. with argon prior to use), purged with argon for at least 20 sec., and sealed with a rubber septum. Using a 50 μL syringe, 50 μL of the CXL-1020 stock solution was injected into each 20 mL vial containing the PBS.

Samples were prepared as follows. In duplicate, 18±1 mg of each sample was accurately weighed into each 4 mL vial. Using an auto pipette, 1 mL of argon-purged anhydrous DMF was added to each 4 mL vial to form a sample stock solution for each sample and the vials were capped and shaken and/or sonicated to insure complete sample dissolution upon visual observation. Using an auto pipette, 20 mL vials were charged with 5 mL of PBS (purged for at least 30 min. with argon prior to use), purged with argon for at least 20 sec., and sealed with a rubber septum. The vials were equilibrated for at least 10 min. at 37° C. in a dry block heater. Thereafter, using a 50 μL syringe, 50 μl of a sample stock solution was injected into each 20 mL vial containing the PBS. The vials were then held at 37° C. in the dry block heater for a time period such that the sum of the time spent in the dry block heater plus the time spent in the automated headspace analyzer oven before sample injection equaled the desired incubation time.

The sequence for auto-injection was as follows: blank replicate 1, blank replicate 2, $N_2O$ standard replicate 1, $N_2O$ standard replicate 2, CXL-1020 standard replicate 1, CXL-1020 standard replicate 2, sample 1 replicate 1, sample 1 replicate 2, sample 2 replicate 1, sample 2 replicate 2, etc., concluding with $N_2O$ standard replicate 3, and $N_2O$ standard replicate 4. An EXCEL spreadsheet is used for inputting data thus determined and calculating, for each sample, the relative $N_2O$ yield in percent for each incubation time. The results obtained are provided in Table 2.

TABLE 2

| | Results of $N_2O$ Headspace Analysis | |
|---|---|---|
| Compound | Relative $N_2O$ Yield (90 minute incubation) | Relative $N_2O$ Yield (360 minute incubation) |
| N-Hydroxy-5-methylfuran-2-sulfonamide (1) | 52% | N/A |
| N-Hydroxy-3-methanesulfonylbenzene-1-sulfonamide (2) | 82% | 94% |

For compounds of formulas (3) and (4), determinations are as described above except enzyme activated samples are also prepared as follows: (i) accurately weigh 50 mg of porcine liver esterase (PLE, E3019-20KU, crude, Sigma-Aldrich) into a 20 mL headspace vial; (ii) using an auto pipette, 5 mL of argon-purged anhydrous PBS is added to form a PLE stock solution; (iii) the vial is capped and shaken to insure complete dissolution upon visual observation; (iv) samples of nitroxyl donors are prepared as disclosed above except 4.75 mL of PBS is added instead of 5 mL; and (v) using an auto pipette, the 20 mL vials are then charged with 250 μmL of PLE stock solution prior to sample addition. The sequence for auto-injection is as follows: blank replicate 1, blank replicate 2, $N_2O$ standard replicate 1, $N_2O$ standard replicate 2, CXL-1020 standard replicate 1, CXL-1020 standard replicate 2, sample 1 (no PLE) replicate 1, sample 1 (no PLE) replicate 2, sample 1 (with PLE) replicate 1, sample 1 (with PLE) replicate 2, sample 2 (no PLE) replicate 1, sample 2 (no PLE) replicate 2, sample 2 (with PLE) replicate 1, sample 2 (with PLE) replicate 2, etc., concluding with $N_2O$ standard replicate 3, and $N_2O$ standard replicate 4.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 µL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride (DTPA), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 µL is introduced into individual thermally-equilibrated headspace vials using a 100 µL gas-tight syringe with a sample-lock to provide final substrate concentrations of 0.1 mM. Substrates are then incubated for 90 minutes or 360 minutes. The headspace (60 µL) is then sampled and injected five successive times into the GC apparatus using the gas-tight syringe with a sample lock. This procedure is repeated for two or more vials per donor.

5.3. Example 4

In Vitro Stability of Nitroxyl Donors in Plasma

Compound (1), compound (2), and CXL-1020 were tested for their stability in plasma. The assay system comprised (i) PBS, or plasma from rat, dog or human (at least 3 donors, male, pooled) at pH 7.4, and (ii) for tests conducted in plasma, an anticoagulant (sodium heparin or sodium citrate). Each test compound (5 µM) was incubated in PBS or plasma at 37° C. on a THERMOMIXER® with shaking Three samples (n=3) were taken at each of seven sampling time points: 0, 10, 30, 60, 90, 180 and 360 minutes. The samples were immediately combined with 3 volumes (i.e., 3 times the volume of PBS or plasma) of acetonitrile containing 1% formic acid and an internal standard to terminate the reaction. AB SCIEX API 3000 LC-MS/MS analysis of the test compounds was performed without a standard curve. Half-lives ($T_{1/2}$) of the test compounds were determined from graphs of the percent remaining values using the peak area response ratio. The half-lives determined are provided in Table 3.

TABLE 3

Half-lives ($T_{1/2}$) of Nitroxyl Donors

| Compound | $T_{1/2}$ (minutes) PBS | $T_{1/2}$ (minutes) Rat | $T_{1/2}$ (minutes) Dog | $T_{1/2}$ (minutes) Human |
|---|---|---|---|---|
| CXL-1020 | 2 | N/A | N/A | 2 |
| N-Hydroxy-5-methylfuran-2-sulfonamide (1) | 68 | 40 | 25 | 65 |
| N-Hydroxy-3-methanesulfonylbenzene-1-sulfonamide (2) | 50 | 20 | 33 | 37 |

For measuring half-lives of compounds of formula (3) or formula (4), a stock solution of pig liver esterase (PLE) is added to the PBS or plasma prior to addition of said compound.

5.4. Example 5

Solubility of Nitroxyl Donors

Initially, the solubilities of the compounds of formula (1) and formula (2) were measured by visual assessment at 100 µg/mL and 1000 µg/mL in a pH 4 buffer. The buffer was prepared by mixing 660 mL of Solution A (10.5023 g of citric acid dissolved in 1 L of water) and 450 mL of Solution B (14.7010 g of sodium citrate tribasic dihydrate dissolved in 1 L of water). The pH of the buffer was 3.98 as measured by pH meter.

Each compound was shaken for about 5 minutes in the pH 4 buffer solution prepared above at two concentration points (100 µg/mL and 1000 µg/mL) and the solubility was observed visually. The results obtained are presented in Table 4.

TABLE 4

Solubility in pH 4 Buffer at 100 µg/mL and 1000 µ/mL

| Compound | Solubility (100 µg/mL) | Solubility (1000 µg/mL) |
|---|---|---|
| N-Hydroxy-5-methylfuran-2-sulfonamide (1) | Y | Y |
| N-Hydroxy-3-methanesulfonylbenzene-1-sulfonamide (2) | Y | Y |

N = Not soluble after shaking for 5 minutes in pH = 4 buffer
Y = Soluble after shaking for 5 minutes in pH = 4 buffer Additionally, a sample of the compound of formula (1) was prepared in water to determine the approximate solubility of the compound in the absence of excipients (e.g., CAPTISOL®). A concentration of approximately 300 mg/mL was achieved, not accounting for the volume contribution of the compound. The pH of the sample was determined to be 2.8, which was adjusted to the target of 4.0 using 0.1 N NaOH. Upon pH adjustment, precipitation of a small amount of solid was observed. The clear solution was diluted in acetonitrile and analyzed by HPLC, resulting in an observed solution concentration of 268 mg/mL. A similar analysis was performed for the compound of formula (2). The compound of formula (2) has a solubility of approximately 10 mg/mL.

5.5 Example 6

Hemodynamic Efficacy of Nitroxyl Donors in Normal and Heart Failure Canines (Tachycardia-Pacing Model)

5.5.1 Materials and Methods

The cardiovascular effects of nitroxyl donors were examined by means of pressure-volume (PV) curve (loops) analysis in conscious, sling-restrained beagle dogs. Animals were allowed free access to drinking water and a commercial canine diet under standard laboratory conditions. Fluorescent lighting was provided via an automatic timer for approximately 12 hours per day. On occasion, the dark cycle was interrupted intermittently due to study-related activities. Temperature and humidity were monitored and recorded daily and maintained to the maximum extent possible between 64° F. and 84° F. and 30% to 70%, respectively. The dogs were acclimated for a period of at least 1 week prior to surgery. Following surgery and recovery the animals were acclimated to sling restraint for a period up to 4.5 hours. Animals were fasted overnight prior to surgery.

Surgical Procedure

Anesthesia

An indwelling venous catheter was placed in a peripheral vein (e.g., cephalic) for administration of anesthetic. General anesthesia was induced intravenously (bolus) with buprenorphine (about 0.015 mg/kg) followed by an intravenous bolus of propofol (about 6 mg/kg). Additionally, a prophylactic antibiotic (cefazolin 20 to 50 mg/kg via i.v.) was given upon induction. A cuffed tracheal tube was placed and used to ventilate mechanically ventilate the lungs with 100% $O_2$ via a volume-cycled animal ventilator (about 12 breaths/minute with a tidal volume of about 12.5 mL/kg) in order to sustain $PaCO_2$ values within the physiological range. Anesthesia was maintained with inhaled isoflurane (1% to 3%).

Cardiovascular Instrumentation

Once a stable (surgical) plane of anesthesia had been established, a left-thoracotomy was performed (under strict aseptic conditions) and each animal was chronically instrumented with sono-micrometry crystals providing left-ventricular (LV) dimensions/volume. Additionally, a fluid-filled catheter and a solid-state monometer were placed in the left ventricle for pressure monitoring. A fluid-filled catheter was placed in the right ventricle (RV) and the aorta (Ao) for pressure monitoring/test article administration. A hydraulic (In-Vivo Metrics) occluder was placed/secured around the inferior vena cava (IVC), in order to allow its controlled constriction for the generation of LV pressure-volume curves during heterometric auto-regulation. The catheters/wires were aseptically tunneled and externalized between the scapulae. Over the course of the study, fluid-filled catheters were regularly (at least once weekly) flushed with a locking-solution in order to prevent both clotting and bacterial growth (2-3 mL of Taurolidine-Citrate solution, TCS-04; Access Technologies).

Pacemaker Implantation

Following the cardiovascular instrumentation, the right jugular vein was carefully exposed and cannulated with a bipolar pacing lead/catheter (CAPSUREFIX® Novus; Medtronic). Under fluoroscopic guidance, this pacing lead was advanced normograde into the right ventricle and actively affixed (screwed in) to the apical endocardium. The proximal end of the lead was secured to the pacing device (Kappa 900; Medtronic). Subsequently, the pacemaker was placed/secured in a subcutaneous pocket in the neck.

Considering that the heart was exposed via a thoracotomy, a bipolar pacing wire was secured in the right ventricular mid-myocardium. This pacing lead was tunneled/externalized between the scapulae, and used in conjunction with an external impulse generator/pacemaker. The implanted endocardial pacemaker was used as a back-up to the external/epicardial pacemaker.

Recovery

Prior to closure of the chest from the thoracotomy, a chest tube was placed for drainage of any fluid and/or gas that accumulated from the surgical procedure. The tube was aspirated twice daily until the amount of fluid removed was less than 35 mL per aspiration in an approximately 24 hour period. The chest tube was then removed.

All animals were administered a prophylactic antibiotic (cefazolin 20 to 50 mg/kg via i.v.) and pain medication (meloxicam at about 0.2 mg/kg via i.v.). If necessary, an additional analgesic was also administered which included a fentanyl patch (25 to 50 mcg/hour). All surgical incisions were closed in layers; the underlying musculature was closed with absorbable sutures and the skin was closed with staples.

Following surgery, the animals were allowed to recover for at least 14 days. Cephalexin (20 to 50 mg/kg) was administered orally BID for at least 7 days and meloxicam (0.1 mg/kg) was administered SID orally or subcutaneously for at least 2 days after surgery. Throughout the recovery phase, the animals were observed daily for routine signs of recovery and the wound sites were observed for any signs of potential infections. Animals experiencing pain, distress and/or infections were brought to the attention of the attending veterinarian and the study director. The skin incision staples were not removed for at least 7 days after surgery.

Induction of Heart Failure

Following a recovery from surgery and/or sufficient washout period from dosing with a nitroxyl donor, animals were subjected to a 3-week overdrive pacing (210 ppm) protocol aimed to trigger left-ventricular dysfunction/remodeling consistent with the heart failure syndrome. In short, via the implanted pacemaker/right-ventricular lead, the ventricle(s) was asynchronously and continuously paced at 210 beats per minute (bpm). Left-ventricular remodeling (and heart failure induction) were confirmed by both echocardiographic (e.g., ejection fraction (EF)) decrease from about 60% to a target of about 35%, left ventricular (LV) dilatation) and neuro-humoral (e.g., N-terminal pro-brain natriuretic peptide (NT proBNP) elevation to greater than 1800 pM/L from a baseline of about 300 pM/L) changes after approximately 3 weeks of pacing. Echocardiographs and blood samples were collected in the absence of pacing (for at least 15 min).

5.5.2 Results

Hemodynamic Efficacy Assessments

The animals (normal or heart failure) were studied during treatment with both vehicle (control) and a nitroxyl donor (either CXL-1020, a compound of formula (1) or a compound of formula (2)). At each dosing period, conscious sling-restrained animals were continuously monitored for up to two to three hours. Following hemodynamic stabilization, infusion of the vehicle was started. Shortly thereafter, left-ventricular pre-load was acutely reduced by means of brief vena cava occlusions (via transient inflation of the vessel occluder) in order to generate a family of pressure-volume curves/loops; up to three occlusions were performed, allowing for hemodynamic recovery between tests. Infusion of the vehicle was continued and after 30 min another (baseline) set of hemodynamic data was collected. Following collection of baseline hemodynamic data, infusion of the nitroxyl donor compound being tested was initiated and derived hemodynamic/functional parameters were obtained/performed at up to four (4) time points selected from the following: at 30, 60, 90, 120, and 180 minutes after the onset of vehicle/test compound infusion. For the placebo or time-control treatment group, each animal was administered an infusion of an appropriate placebo for up to 180 minutes. In all cases, the test compound was delivered at a constant intravenous infusion rate of 1 mL/kg/hr and was compared at a molar equivalent dose rate.

The resulting left-ventricular pressure and volume data were analyzed in order to generate relationships representing the contractile and energetic state of the myocardium. Systolic arterial pressure (SAP), diastolic arterial pressure (DAP), and mean arterial pressure (MAP) were collected. Left-ventricular mechanical and/or geometrical indices were obtained from the pressure (ESP, EDP, dP/dt max/min, time-constant of relaxation-tau [based on mono-exponential decay with non-zero asymptote]) and volume (end-systolic volume (ESV), end diastolic volume (EDV), stroke volume (SV)) signal. In addition, the following measurements were derived from left-ventricular pressure-volume data (PV loops) generated during brief periods of preload reduction: pressure volume area (PVA) and stroke work (SW), end-systolic (ESPVR) and end-diastolic (EDPVR) pressure volume relationships, and end systolic pressure and stroke volume relationship (arterial elastance (Ea)). Representative data obtained from studies in normal dogs and heart failure dogs is shown in Table 5 and Table 6, respectively. A SVR (systemic vascular resistance) decrease correlates with vasodilation.

TABLE 5

Hemodynamic Parameters for Nitroxyl Donors in Normal Canines (% Change from Baseline)

| | Compound | | | |
|---|---|---|---|---|
| | Control | CXL-1020 | (1) | (2) |
| Dose Rate (μmol/kg/min) | 0 | 100 | 50 | 100 |
| Number of Animals | 3 | 6 | 8 | 4 |
| HR | −2.21 ± 1.51 | 6.71 ± 4.72 | −4 ± 2 | −6.17 ± 5.58 |
| ESP | −1.8 ± 0.58 | −17.79 ± 3.09 | −18 ± 2 | −15.22 ± 2.39 |
| EDV | 2.62 ± 0.42 | −20.51 ± 7.63 | −6 ± 2 | −17.41 ± 1.58 |
| Tau | 11.14 ± 1.15 | −6.58 ± 4.53 | −6 ± 1 | −6.40 ± 7.11 |
| SW | −2.80 ± 1.26 | −13.96 ± 5.51 | −11 ± 4 | −17.56 ± 2.66 |
| ESPVR | −3.20 ± 1.15 | 28.25 ± 8.69 | 19 ± 1 | 25.87 ± 5.04 |
| PRSW | −0.78 ± 0.38 | 12.60 ± 2.96 | 12 ± 1 | 12.88 ± 1.12 |

Abbreviations:
HR: Heart rate. Increased HR, either due to reflex response to low blood pressure or due to a primary drug effect on the heart, is bad.
ESP: End systolic pressure - similar to MAP below.
EDP or LVEDP: End diastolic pressure (left ventricular). Correlates with pulmonary pressures. A decrease indicates a reduction of pulmonary congestion (a key objective of acute heart failure therapy).
Tau: An index of lusitropy, or relaxation of the heart during diastole. Decrease is positive and indicates improved diastolic performance.
SW: Stroke work. Measure of how much work the heart exerts to create a given amount of forward flow.
ESPVR: End systolic pressure volume relationship. A measure of inotropy/contractility (a key objective of acute heart failure therapy). Increases indicate improved cardiac performance and efficiency.
PRSW: Preload recruitable stroke work - similar to ESPVR above.
SV: Stroke volume. The amount of blood ejected from the left ventricle with each beat of the heart. An inotrope should increase this, given identical loading conditions.
MAP OR MBP: Mean arterial pressure or mean blood pressure. Small drops are positive and evidence of vasodilation.
EDV or LVEDV: End diastolic volume (left ventricular). Index of the degree of filling in diastole. A decrease indicates a reduction in volume overload.

TABLE 6

Hemodynamic Parameters for Nitroxyl Donors in Heart Failure Canines (% Change from Baseline)

| | Compound | | | |
|---|---|---|---|---|
| | Control | CXL-1020 | (1) | (2) |
| Dose Rate (μmol/kg/min) | 0 | 100 | 75 | 100 |
| Number of Animals | 3 | 6 | 6 | 4 |
| HR | −5.08 ± 5.83 | −0.23 ± 2.25 | −6 ± 2 | −1.36 ± 2.06 |
| ESP | 3.89 ± 2.11 | −14.78 ± 3.24 | −17 ± 1 | −13.83 ± 3.30 |
| EDV | 0.86 ± 0.86 | −12.03 ± 3.72 | −9 ± 2 | −3.26 ± 1.05 |
| Tau | 4.05 ± 4.72 | −17.27 ± 1.39 | −16 ± 4 | −12.51 ± 2.72 |
| SW | 1.83 ± 1.87 | −12.01 ± 4.24 | −9 ± 2 | −9.41 ± 2.84 |
| ESPVR | −3.14 ± 0.87 | 45.42 ± 16.48 | 29 ± 1 | 22.84 ± 5.69 |
| PRSW | −0.88 ± 0.68 | 21.97 ± 3.79 | 22 ± 1 | 17.91 ± 1.47 |

Abbreviations:
HR, heart rate;
ESP, end systolic pressure;
EDV, end diastolic volume;
Tau, time constant for relaxation;
SW, stroke work;
ESPVR, end systolic pressure volume relationship;
PRSW, preload recruitable stroke work.

FIG. 1 shows the hemodynamic profile 180 minutes after administration of CXL-1020 and two compounds of the disclosure (compounds of formula (1) and formula (2)) using a tachycardia-pacing model of heart failure. Each compound was administered intravenously at a rate of 100 μg/kg/min. FIG. 2 shows the hemodynamic profile of the compound of formula (1) at various dosages using a tachycardia-pacing model of heart failure. The results demonstrate that compounds of formula (1) and (2) have comparable hemodynamic activity to CXL-1020 in both normal and failing canine models. In particular, the compounds of formula (1) and (2) produce significant enhancement of inotropy and lusitropy, and modest reductions in blood pressure.

5.6 Example 7

Hemodynamic Efficacy of Nitroxyl Donors in Heart Failure Canines (Canine Microembolization Heart Failure Model)

5.6.1 Materials and Methods

Heart failure was produced using healthy, conditioned, purpose-bred mongrel dogs (20-26 kg) using a sequential microembolization model. Coronary microembolization was performed until LV-ejection fraction (determined angiographically under anesthesia) was approximately 30% or lower. Two weeks were then provided after the last microembolization to ensure stabilization of each animal prior to initiating experiments.

An initial dose-finding study (2-100 μg/kg/min for 40 min) was performed in 3 dogs to identify therapeutically relevant doses of a compound of formula (1). Based on these data, a primary group of six animals were studied, receiving 3 or 10 μg/kg/min of a compound of formula (1) over a 4 hour period, followed by one hour washout. Only one dose was studied on a given day, the other at least one-week later, and the order randomized. Hemodynamic, ventriculographic, and echocardiographic measurements were made during left and right heart catheterizations in anesthetized dogs (induction: hydromorphone (0.22 mg/kg i.v.) and diazepam (0.17 mg/kg i.v.), maintenance: 1-2% isofluorane).

LV end-systolic volume (ESV) and end-diastolic volumes (EDV) were calculated from ventriculograms using the area-length method. Peak aortic blood velocity was obtained in the ascending aorta using flow Doppler for measurements of peak power index (PPI). LV fractional area of shortening (FAS) was measured from LV short axis view at the level of papillary muscles obtained from 2-dimensional echocardiograms. Measured indexes of LV diastolic function included deceleration time of mitral inflow velocity (DT), ratio of the integral of early mitral inflow velocity (Ei) to velocity during atrial contraction (Ai) (Ei/Ai) and LV end-diastolic circumferential wall stress (EDWS).

Measurements of myocardial oxygen consumption were performed at baseline and at 4 hours after 10 μg/kg/min infusion. Specifically, arterial and coronary sinus blood samples were simultaneously drawn at baseline and at the end of each study time point. Oxygen content was determined with a hemoximeter. Coronary artery blood velocity was measured with a Doppler flow velocity wire placed in the left circumflex coronary artery proximal to the first marginal branch or in the left anterior descending coronary artery just proximal to the first diagonal branch. Blood flow was estimated by calculating the cross-sectional area of the coronary artery at the site of the velocity measurement from coronary angiography. Total coronary blood flow was assumed to be twice the flow measured in the circumflex or left anterior descending coronary artery. Oxygen consumption of the left ventricle (MVO2) was calculated as the product of total coronary blood flow and the oxygen content difference between arterial and coronary sinus blood.

5.6.2 Results

Hemodynamic Efficacy Assessments

The animals were studied during treatment with both vehicle and a nitroxyl donor. FIG. 3 shows the hemodynamic profile of the compound of formula (1) following induction of heart failure in dogs evaluated using a canine microembolization heart failure model. The data is shown for final time point during infusion at two rates of infusion. The results demonstrated that the compound of formula (1) had comparable hemodynamic activity to CXL-1020.

5.7 Toxicological Studies with Nitroxyl Donors 5.7.1 Example 8

In Vivo Trials with CXL-1020

During in vivo trials of the nitroxyl donor, CXL-1020 (N-hydroxy-2-methanesulfonylbenzene-1-sulfonamide), a 14-day study was conducted to evaluate tolerance in dogs treated with continuous infusions of CXL-1020 at dose rates of up to 90 µg/kg/min. This first study found that CXL-1020 was tolerated when administered at a dose rate of 60 µg/kg/min. Unexpectedly, however, clinical pathology changes consistent with an inflammation process, as reflected in changes in clinical pathology markers of inflammation, were observed at the 60 µg/kg/min dose rate. To further investigate this undesirable side-effect, a follow-up 14-day study in dogs was initiated. The follow-up study needed to be terminated after only 4 days due to the appearance of other undesirable side-effects: the unexpected occurrence of significant swelling and inflammation in the dogs' hind limbs where infusion catheters had been surgically implanted, which occasionally interfered with normal limb function; skin discoloration in the inguinal region; decreased activity; inappetance; and in the highest-dosage group, skin cold to the touch.

To determine the cause of the inflammation and hind limb swelling, a series of 72-hour continuous infusion investigative studies were conducted over the following 6 months. The results of those studies showed that CXL-1020, when administered in a pH 4 formulation of a 1:1 molar ratio of CXL-1020:CAPTISOL®, diluted into a solution of 5% dextrose in water, caused clinical pathology changes consistent with an inflammatory process at dose rates greater than or equal to 0.03 µg/kg/min in dogs. Vascular inflammation was observed around the site of insertion of the catheter into the femoral vein (15 cm upstream from the catheter tip), at the catheter tip, and downstream from the catheter tip. The first site of inflammation, the catheter insertion site, caused the dog hind limb swelling and inflammation observed in the early-terminated follow-up study. Increasing infusate pH from 4 to 6 decreased inflammation, improving the inflammatory profile by approximately 3-fold. However, significant undesirable side effects were still demonstrated when CXL-1020 was administered at dose rates greater than or equal to 3 µg/kg/min in the dogs.

To avoid the catheter insertion site-associated side effects and to assess whether the vascular inflammation was due to the design of the implanted catheter, a 24-hour continuous infusion study was conducted in dogs using a percutaneous catheter placed in a peripheral (cephalic) vein. After 6 hours of infusion, significant edema was observed in the upper forelimb, downstream from the catheter tip. After 24 hours of infusion, clinical pathology changes similar to those observed in previous studies using an implanted central catheter were detected. Also detected was microscopic pathology demonstrating a severe thrombophlebitis at the catheter tip and progressing with a gradient of lessening severity downstream from the catheter tip.

To determine whether a local phlebitis would occur in humans upon longer duration dosing, a longer duration study was conducted in healthy volunteers. The longer duration study included a dose escalation study in which cohorts of 10 volunteers were to be sequentially administered a 24-hour continuous infusion of CXL-1020 at the dose rates of 10, 20, and 30 µg/kg/min with a safety assessment between each cohort. Each cohort consisted of 2 placebo and 8 active treatments with a sentinel pair of 1 active and 1 placebo followed by the main group of 1 placebo and 7 active treatments. The infusion was via a percutaneous catheter inserted into a forearm vein. The catheter was switched to the contralateral arm after 12 hours of infusion. The dose rate of 10 µg/kg/min for 24-hours was found to be well tolerated. In the second cohort, administered a dose of 20 µg/kg/min for 24-hours, there were no adverse findings in the 2 placebo-treated volunteers but there were mild findings (either clinical signs and/or changes in clinical pathology) in all 8 subjects consistent with infusion site phlebitis. Based on these results, the longer duration safety study was halted.

Exploratory studies were continued to determine the cause of the undesirable side effects of CXL-1020 at the higher, but still clinically desirable, doses. Studies conducted with the byproduct of CXL-1020, the moiety that remains after nitroxyl donation, was negative, indicating that the CXL-1020's side effects were attributable to either the parent compound, CXL-1020, or to the HNO produced therefrom. Studies were conducted with alternative nitroxyl donors that were structurally unrelated to CXL-1020 but had similar half-lives for nitroxyl donation (half-lives of about 2 minutes). For these donors, nitroxyl was at its highest intravascular concentration at the catheter tip and immediately downstream in the vein into which the catheter had been inserted. In all instances, local vascular side effects at the catheter tip were observed. These results suggested that the inflammation was caused by nitroxyl that was rapidly released from the short half-life nitroxyl donors.

5.7.2 Example 9

Compounds of the Disclosure Possess an Improved Toxicological Profile Relative to CXL-1020

Studies were conducted in male and female beagle dogs. Animals were allowed free access to drinking water and a commercial canine diet under standard laboratory conditions. Animals were fasted prior to blood sample collections when indicated by the study protocol. Fluorescent lighting was provided via an automatic timer for approximately 12 hours per day. On occasion, the dark cycle was interrupted intermittently due to study-related activities. Temperature and humidity were monitored and recorded daily and maintained to the maximum extent possible between 64° F. to 84° F. and 30% to 70%, respectively. The dogs were acclimated for a period of at least 1 week. During this period, the animals were weighed weekly and observed with respect to general health and any signs of disease. The animals were acclimated to wearing a jacket for at least three days prior to dose administration. Additionally, the animals were also acclimated to wearing an Elizabethan collar (e-collar) during the jacket acclimation.

Surgical Procedure and Dosing Procedure

Animals were catheterized the day prior to dose administration. A percutaneous catheter was placed (using aseptic technique and sterile bandaging) in the cephalic vein distal to the elbow. The animals were free-moving in their cages during continuous infusion dose administration. To facilitate continuous infusion dose administration, the peripheral catheter was attached to an extension set routed underneath a canine jacket and then attached to a tether infusion system. To prevent the animals from accessing/removing the peripherally placed percutaneous catheter, the catheterization site was bandaged using Vet Wrap and an e-collar was placed on the animals for the duration of the treatment (i.e., the catheterized period). During the pretreatment period, the venous catheter was infused continuously at a rate of approximately 2-4 mL/hr with 0.9% sodium chloride for injection, USP (saline) to maintain catheter patency. Prior to dosing, the infusion system was pre-filled (slow bolus infusion) with the respective dosing solution to ensure that dosing began as soon as the infusion pump was started. The infusion line was connected to a reservoir containing the control or test compound and the infusion was started. Test compositions were infused continuously, at a predetermined constant infusion rate (1 or 2 mL/kg/hr), for 24 hours and were compared at molar equivalent dose rates.

Clinical Observations, Clinical Pathology, and Microscopic Pathology

A detailed clinical examination of each animal was performed twice daily and body temperature measurements and blood samples for clinical pathology were collected from all animals pre-dose and 6 hours, 12 hours, 24 hours and 72 hours post start of composition infusion. At the termination of the study, all animals were euthanized at their scheduled necropsy and complete necropsy examinations were performed. Selected tissues were collected, fixed and stored for potential future microscopic examination. The cephalic vein containing the infusion catheter was dissected intact along with the brachial vein and examined along its entire length. The location of the catheter tip was marked on the unfixed specimen. After fixation, the specimen was trimmed and processed to slide to provide transverse histologic sections representing the catheter tip and surrounding tissues both proximal and distal to the catheter tip (i.e., 1 cm distal to the catheter tip, at the catheter tip, and 1, 5, 10, 15, and 20 cm proximal to the catheter tip). Relative to the catheter tip, "proximal" was defined as closer to the heart and "distal" was defined as further from the heart.

Safety Assessment

Clinical pathology changes consistent with an inflammatory syndrome were observed at some dose rates of compounds of formula (1), formula (2) and CXL-1020. Each compound was formulated with CAPTISOL® (7% w/v) in sterile water at a pH of 4. The most sensitive biomarkers of the inflammation were: (1) white cell count (WBC, obtained as (number of white blood cells)/μL by multiplying the values in the rightmost portion of FIG. 4 by 103), (2) fibrinogen concentration (given in mg/dL in the rightmost portion of FIG. 4), and (3) C-Reactive Protein (CRP) concentration (given in mg/L in the rightmost portion of FIG. 4). The severity of the changes was dependent on the identity of the compound and the dose rate at which the compound was administered (FIG. 4). In FIG. 4, a score ranging from 0 (low severity) to 2 (high severity) was assigned to each of these biomarkers of inflammation according to the rightmost portion in that figure. A cumulative score was calculated from the sum of these marker scores. The NOAELs, determined based on these clinical pathology markers and expressed in molar equivalent dose rates (μg/kg/min) to CXL-1020, are provided in Table 7.

TABLE 7

No Observed Adverse Effect Levels (NOAEL) of Nitroxyl Donors

| Compound | NOAEL (μg/kg/min) |
|---|---|
| N-Hydroxy-2-methanesulfonylbenzene-1-sulfonamide (CXL-1020) | <0.03 |
| N-Hydroxy-5-methylfuran-2-sulfonamide (1) | >20 |
| N-Hydroxy-3-methanesulfonylbenzene-1-sulfonamide (2) | 3 |

For CXL-1020, significant elevations in WBC, fibrinogen and CRP were observed, even at concentrations as low as 0.03 μg/kg/min. The compound of formula (1) and the compound of formula (2) each have a NOAEL at doses significantly higher than that of CXL-1020. The compound of formula (1) has the most favorable toxicological profile, showing no adverse effects at doses at least as high as 20 μg/kg/min. This represents greater than a 660-fold improvement relative to CXL-1020.

Collectively, these findings suggest that CXL-1020 infusion causes an inflammatory syndrome, which is substantially reduced with the compound of formula (1) and the compound of formula (2).

The findings suggested that the undesirable vascular side effects associated with CXL-1020 at the catheter tip, downstream of the catheter tip and in certain circumstances, upstream of the catheter tip, were due to local inflammation caused by nitroxyl release. Moreover, it was postulated that inflammation can be significantly mitigated at these sites using longer half-life nitroxyl donors. Confirmation was obtained through evaluating the nitroxyl donors through detailed histopathology of the vasculature at the site of insertion of into the femoral vein (15 cm distal to the catheter tip), along the catheter track to the catheter tip, and past the tip downstream 20 cm. Microscopic pathology findings of edema, hemorrhage, vascular inflammation and perivascular inflammation were determined at particular dose rates of the nitroxyl donors.

FIG. 5 depicts a "heat-map" showing a composite lab score for the microscopic pathology findings in which the severity of vascular inflammation, hemorrhage, thrombus and vascular degeneration/regeneration was scored in sections of the vasculature as described above. Findings of (1) edema, (2) vascular and perivascular inflammation, and (3) hemorrhage were scored (each assigned a value selected from: 0=within normal limits; 1=minimal; 2=mild; 3=moderate; 4=severe) in sections of the vessel beginning 1 cm distal (upstream) from the catheter tip progressing 20 cm proximal (downstream) from the catheter tip. A composite lab score was calculated from the sum of these findings scores. In FIG. 5, the cumulative histology composite lab score ranges from 0-2 (low severity) to 11-12 (high severity). The severity of the microscopic changes and the distance from the catheter tip in which they were detected was observed to be dependent on the identity of the nitroxyl donor and the dose rate at which the nitroxyl donor was administered. The NOAEL values determined based on these microscopic pathology markers for a series of nitroxyl donors, expressed in molar equivalent dose rates (μg/kg/min) to CXL-1020, are provided in Table 8.

TABLE 8

No Observed Adverse Effect Levels (NOAEL) of Nitroxyl Donors

| Compound | NOAEL (μg/kg/min) |
|---|---|
| N-Hydroxy-2-methanesulfonylbenzene-1-sulfonamide (CXL-1020)) | <3 |
| N-Hydroxy-5-methylfuran-2-sulfonamide (1) | ≥180 |
| N-Hydroxy-3-methanesulfonylbenzene-1-sulfonamide (2) | ≥180 |

The findings presented in Table 8 provide additional evidence that the compounds of formula (1) and (2) have a substantially improved toxicological profile relative to CXL-1020. The vascular side effects at any dose decreased in severity as a function of distance from the catheter tip, and the severity of such vascular side effects decreased with decreasing dose. These findings confirmed a large safety margin for compounds of formulas (1) and (2), which translate into a substantial therapeutic index in humans, and suitability for intravenous administration at therapeutically effective doses and dosage rates.

5.8 Stability of Intravenous Dosing Solutions

5.8.1 Example 10

Compound of Formula (1)—Dosing Solution Stored at 25° C.

The stability of dosing solutions of the compound of formula (1) prepared from a CAPTISOL® concentrate diluted into commercially-available IV diluents was assessed at 25° C. over 48 hours, with analysis points at 0, 8, 12, 16, 24, and 48 hours after dilution. Due to the analysis points required, two studies were executed with separate sets of dosing solutions. The first (group A) encompassed all time points except that at 16 hours. The second (group B) entailed analysis at 0 and 16 hours only. The concentrates used to prepare the two sets of dosing solutions were prepared from two separate vials of the same lot of lyophilized drug product (24 mg/mL compound of formula (1)/30% CAPTISOL®).

Concentrate Preparation

One vial of lyophilized drug product (24 mg/mL Compound of formula (1)/30% CAPTISOL®, pH 4) was reconstituted with 10 mL of water for injection (WFI) quality water to prepare each concentrate (for dosing solution groups A and B). The pH values of the resultant solutions were measured, and were determined to be approximately 3.9 for both vials. No pH adjustment was performed. The concentrates were diluted and analyzed by HPLC (XBridge Phenyl Column (Waters); UV absorbance detector at 272 nm; mobile phase a step gradient of aqueous acetonitrile containing 0.1% (v/v) formic acid), and both were determined to contain 20-21 mg/mL of the compound of formula (1), rather than the nominal value of 24 mg/mL, ostensibly due to contribution of the dissolved API and CAPTISOL® to the total solution volume.

Diluent Preparation

Commercially-available potassium acetate and potassium phosphate solutions were selected for evaluation. Potassium acetate was obtained commercially, and a USP potassium phosphate solution was prepared according to the Hospira product insert for the commercial product. Each solution was diluted to 10 mM in 5% dextrose (D5W) and 2.5% dextrose (D2.5W). Commercially-available D5W was diluted 2-fold with WFI quality water to produce the D2.5W solution. The pH of each concentrated and diluted solution was measured; the results are presented in Table 9.

TABLE 9

Results of pH Measurement of Selected Diluents

| Diluent | Concentration | pH |
|---|---|---|
| Acetate | 10 mM in D2.5W | 6.2 |
|  | 10 mM in D5W | 6.0 |
|  | Initial (2M) | 6.7 |
| Phosphate | 10 mM in D2.5W | 6.8 |
|  | 10 mM in D5W | 6.7 |
|  | Initial (3M) | 6.5 |

Dosing Solution Preparation

The compound of formula (1) concentrate was diluted volumetrically on a 5 mL scale into the 10 mM diluent solutions to achieve concentrations of 8, 1, and 0.1 mg/mL of the compound of formula (1), as summarized in Table 10. Each sample was prepared in duplicate. The dextrose content in the 10% CAPTISOL® solution was reduced to ensure that the dosing solutions were substantially isotonic. Each solution was stored at 25° C.

TABLE 10

Preparation of Dosing Solutions for Stability Evaluation

| Compound of Formula (1) (mg/mL) | Diluent | Dilution factor | CAPTISOL® (% w/v) |
|---|---|---|---|
| 8.0 | 10 mM acetate or phosphate in D2.5W | 3 | 10% |
| 1.0 | 10 mM acetate or phosphate | 24 | 1.3% |
| 0.1 | in D5W | 240 | 0.1% |

Sample Analysis

Samples were analyzed upon preparation and after 8, 12, 16, 24, and 48 hours of storage at 25° C. The visual appearance of each sample was noted, the pH was measured, and each sample was analyzed by HPLC for concentration and presence of the major degradant, the compound of formula (5), depicted below, formed after the release of the HNO group.

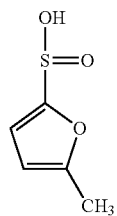

(5)

Results

The results of the stability evaluation are presented in Table 11, Table 12 and Table 13. The presence of a peak corresponding to the degradant (compound of formula (5)) in a sample is denoted by an "X".

The results were generally consistent for each duplicate within a pair and between corresponding dosing solutions prepared in groups A and B. A difference in recovery was observed between duplicates at the 24 and 48 hour time points for the samples prepared to contain 0.1 mg/mL of the compound of formula (1) in phosphate.

Complete recovery (within the accuracy of the HPLC method) and absence of a detectable amount of a compound of formula (5) peak was maintained over 48 hours for the samples prepared to 8 mg/mL of the compound of formula (1) in acetate- and phosphate-based diluents. These samples actually contained approximately 7 mg/mL of the compound of formula (1), consistent with the concentration of 20-21 mg/mL compound of formula (1) in the concentrate. In both diluents, stability was superior in the samples prepared to 8 mg/mL compound of formula (1) than in the samples prepared to lower concentrations. Without being bound by theory, the better stability of these samples compared to those prepared to lower concentrations of the compound of formula (1) may be attributed to the higher CAPTISOL® concentration (10% in the diluted solutions).

All samples remained clear and colorless over the 48 hours of storage. The pH of all samples decreased over time. The known degradant (compound of formula (5)) was observed at t0 (immediately following preparation of the sample) in all samples prepared to contain 0.1 mg/mL of the compound of formula (1) and at all subsequent time points in all samples prepared to contain 0.1 mg/mL and 1 mg/mL of the compound of formula (1).

In general, stability decreased with decreasing concentration of the compound of formula (1). Without being bound by theory, the decreased stability was likely due to the lower percent CAPTISOL® in the dosing solutions. The initial extent of degradation (through 16 hours) was similar in the samples prepared to contain 0.1 mg/mL of the compound of formula (1) in the acetate- and phosphate-based diluents. However, the stability of the samples prepared to contain 1 mg/mL demonstrated significantly better stability in acetate than in phosphate.

TABLE 11

Results of Dosing Solution Stability Evaluation at 25° C., Percent Recovery

| Dosing Solution | Duplicate | Diluent | Compound of Formula (1) mg/mL | Compound of Formula (1) mg/mL t0 (group A) | Compound of Formula (1) mg/mL t0 (group B) | Recovery from t0 8 h (A) | 12 h (A) | 16 h (B) | 24 h (A) | 48 h (A) |
|---|---|---|---|---|---|---|---|---|---|---|
| 1 | a | 10 mM acetate in D2.5W | 8.0 | 6.94 | 7.06 | 101% | 102% | 101% | 102% | 101% |
|  | b |  |  | 6.95 | 7.06 | 101% | 102% | 101% | 102% | 103% |
| 2 | a | 10 mM acetate in D5W | 1.0 | 0.86 | 0.85 | 97% | 97% | 97% | 94% | 92% |
|  | b |  |  | 0.87 | 0.84 | 98% | 98% | 98% | 96% | 95% |
| 3 | a | 10 mM acetate in D5W | 0.1 | 0.10 | 0.09 | 81% | 78% | 66% | 67% | 55% |
|  | b |  |  | 0.10 | 0.09 | 80% | 75% | 68% | 63% | 51% |
| 4 | a | 10 mM phosphate in D2.5W | 8.0 | 6.98 | 6.79 | 98% | 99% | 102% | 99% | 100% |
|  | b |  |  | 7.00 | 6.93 | 99% | 94% | 100% | 100% | 100% |
| 5 | a | 10 mM phosphate in D5W | 1.0 | 0.87 | 0.85 | 89% | 86% | 86% | 78% | 71% |
|  | b |  |  | 0.88 | 0.85 | 90% | 83% | 82% | 79% | 72% |
| 6 | a | 10 mM phosphate in D5W | 0.1 | 0.10 | 0.10 | 83% | 78% | 72% | 62% | 41% |
|  | b |  |  | 0.10 | 0.10 | 79% | 72% | 68% | 50% | 32% |

TABLE 12

Results of Dosing Solution Stability Evaluation at 25° C., pH

| Dosing Solution | Duplicate | Diluent | Compound of Formula (1) mg/mL | pH t0 (group A) | t0 (group B) | 8 h (A) | 12 h (A) | 16 h (B) | 24 h (A) | 48 h (A) |
|---|---|---|---|---|---|---|---|---|---|---|
| 1 | a | 10 mM acetate in D2.5W | 8.0 | 5.6 | 5.5 | 5.4 | 5.4 | 5.4 | 5.4 | 5.3 |
|  | b |  |  | 5.6 | 5.5 | 5.5 | 5.4 | 5.4 | 5.3 | 5.3 |
| 2 | a | 10 mM acetate in D5W | 1.0 | 5.7 | 5.7 | 5.6 | 5.7 | 5.5 | 5.5 | 5.3 |
|  | b |  |  | 5.9 | 5.7 | 5.7 | 5.8 | 5.5 | 5.5 | 5.4 |
| 3 | a | 10 mM acetate in D5W | 0.1 | 6.1 | 5.9 | 5.9 | 5.9 | 5.4 | 5.7 | 5.7 |
|  | b |  |  | 5.8 | 5.9 | 5.9 | 5.9 | 5.3 | 5.7 | 5.5 |
| 4 | a | 10 mM phosphate in D2.5W | 8.0 | 6.3 | 6.1 | 5.9 | 5.9 | 5.6 | 5.5 | 5.0 |
|  | b |  |  | 6.3 | 6.2 | 5.9 | 5.8 | 5.6 | 5.5 | 4.7 |
| 5 | a | 10 mM phosphate in D5W | 1.0 | 6.5 | 6.6 | 6.3 | 6.4 | 6.2 | 6.1 | 5.8 |
|  | b |  |  | 6.6 | 6.5 | 6.3 | 6.4 | 6.1 | 6.3 | 6.0 |
| 6 | a | 10 mM phosphate in D5W | 0.1 | 6.8 | 6.7 | 6.6 | 6.6 | 6.3 | 6.5 | 6.4 |
|  | b |  |  | 6.8 | 6.8 | 6.5 | 6.5 | 6.2 | 6.5 | 6.4 |

TABLE 13

Results of Dosing Solution Stability Evaluation at 25° C. - Measuring Appearance of Compound of Formula (5)

| Dosing Solution | Duplicate | Diluent | Compound of Formula (1) mg/mL | t0 (group A) | Compound of Formula (5) t0 (group B) | 8 h (A) | 12 h (A) | 16 h (B) | 24 h (A) | 48 h (A) |
|---|---|---|---|---|---|---|---|---|---|---|
| 1 | a | 10 mM acetate in D2.5W | 8.0 | | | | | | | |
| | b | | | | | | | | | |
| 2 | a | 10 mM acetate in D5W | 1.0 | | | X | X | X | X | X |
| | b | | | | | X | X | X | X | X |
| 3 | a | 10 mM acetate in D5W | 0.1 | X | X | X | X | X | X | X |
| | b | | | X | X | X | X | X | X | X |
| 4 | a | 10 mM phosphate in D2.5W | 8.0 | | | | | | | |
| | b | | | | | | | | | |
| 5 | a | 10 mM phosphate in D5W | 1.0 | | | X | X | X | X | X |
| | b | | | | | X | X | X | X | X |
| 6 | a | 10 mM phosphate in D5W | 0.1 | X | X | X | X | X | X | X |
| | b | | | X | X | X | X | X | X | X |

5.8.2 Example 11

Compound of Formula (1)—Dosing Solution Stored at 2° C.-8° C. Followed by Storage at 25° C.

The stability of dosing solutions of the compound of formula (1) prepared from a CAPTISOL® concentrate diluted into commercially available IV diluents was prepared as described in Example 10. The solutions were assessed at 2° C.-8° C. over 24 hours followed by storage at 25° C. over 48 hours. As shown in Table 14, recoveries of the compound of formula (1) were generally higher than for the corresponding samples stored at 25° C. for all dosing solutions (see Table 12 from previous example), suggesting improved stability for dosing solutions prepared and stored at 2° C.-8° C. prior to storage at 25° C.

5.8.3 Example 12

Compound of Formula (2)—Dosing Solution Stored at 25° C.

A series of dosing solutions of the compound of formula (2) for IV administration was assessed. The selected concentrate of compound of formula (2), prepared at 30 mg/mL in a vehicle of 30% CAPTISOL® at pH 4.0, was evaluated at low, mid, and high concentrations (0.1, 1 and 5 mg/mL, respectively) upon dilution into various dosing solutions. For dilution of the compound of formula (2) to 0.1 and 1 mg/mL, three dosing solutions were evaluated: (1) D5W, (2) D5W with 5 mM K-phosphate (pH=6), and (3) D5W with 20 mM K-phosphate (pH=6). To maintain iso-osmolality for dilutions of the compound of formula (2) to 5 mg/mL, the concentration of dextrose in the dosing solutions was reduced to 2.5% (w/v).

TABLE 14

Results of Dosing Solution Stability Evaluation at 2° C.-8° C. and 25° C., Percent Recovery

| Sample # | Diluent | Compound of Formula (1) mg/mL | t0 (group A) 2-8° C. | t0 (group B) 2-8° C. | 24 h (A) 2-8° C. | 24 h (B) 2-8° C. | 32 h (A) 8 h at 25° C. | 36 h (A) 12 h at 25° C. | 40 h (B) 16 h at 25° C. | 48 h (A) 24 h at 25° C. | 72 h (A) 48 h at 25° C. |
|---|---|---|---|---|---|---|---|---|---|---|---|
| 1 | 10 mM acetate in D2.5W | 8.0 | 7.13 | 6.91 | 99% | 103% | 101% | 99% | 103% | 97% | 99% |
| 2 | 10 mM acetate in D5W | 1.0 | 0.89 | 0.89 | 99% | 100% | 98% | 98% | 93% | 95% | 92% |
| 3 | 10 mM acetate in D5W | 0.1 | 0.10 | 0.10 | 97% | 97% | 92% | 89% | 67% | 82% | 73% |
| 4 | 10 mM phosphate in D2.5W | 8.0 | 7.18 | 7.08 | 100% | 102% | 99% | 99% | 100% | 97% | 97% |
| 5 | 10 mM phosphate in D5W | 1.0 | 0.89 | 0.88 | 99% | 101% | 95% | 93% | 90% | 87% | 81% |
| 6 | 10 mM phosphate in D5W | 0.1 | 0.11 | 0.10 | 97% | 97% | 89% | 86% | 76% | 76% | 63% |

Thus, the dosing solutions evaluated were: (1) D2.5W, (2) D2.5W with 5 mM K-phosphate (pH=6), and (3) D2.5W with 20 mM K-phosphate (pH=6).

The potential dosing solutions were assessed for visual appearance, pH, osmolality, and concentration and purity by HPLC (XBridge Phenyl Column (Waters); UV absorbance detector at 272 nm; mobile phase a step gradient of aqueous acetonitrile containing 0.1% (v/v) formic acid) after approximately 0, 16, 24, and 48 hours of storage at 25° C. All samples were clear, colorless solutions—with the sole exception of 5 mg/mL of the compound of formula (2) in D2.5W with 5 mM phosphate which had a clear, light yellow appearance after 48 hours at 25° C. All solutions were iso-osmotic (290+/−50 mOsm/kg)—with the sole exception of 1 mg/mL of the compound of formula (2) in D5W with 20 mM phosphate which had an osmolality of approximately 350 mOsm/kg. Furthermore, with the sole exception of 5 mg/mL of the compound of formula (2) in D2.5W with 5 mM phosphate, all other dosing solutions sustained the compound of formula (2) at the target concentrations of 0.1, 1 and 5 mg/mL over 48 hours.

In addition, the known degradant, the compound of formula (6), which is depicted below, formed after release of the active nitroxyl group, was observed after 16 hours at 25° C. in small quantities by HPLC in the dosing solutions containing phosphate buffer.

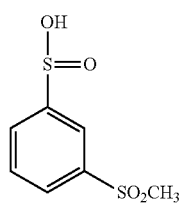

(6)

The observed amount of the compound of formula (6) was on the order of the limit of detection of the method.

The stability of 5 mg/mL of the compound of formula (2) dosing solutions was further evaluated as a function of pH and buffer. A concentrated solution of the compound of formula (2), prepared at 30 mg/mL in a vehicle of 30% CAPTISOL® at pH 4.0, was diluted to 5 mg/mL into four potential dosing solutions. The four dosing solutions were evaluated: (1) D2.5W, 5 mM K-phosphate (pH=6.0), (2) D2.5W with 5 mM K-citrate (pH=6.0), (3) D2.5W, 5 mM K-citrate (pH=5.0), and (4) D2.5W, 5 mM K-acetate (pH=5.0). All dosing solutions of the compound of formula (2) were iso-osmotic (290+/−50 mOsm/kg). After approximately 24 and 48 hours of storage at 25° C., the dosing solutions were assessed for visual appearance, pH, and concentration and purity by HPLC. The non-phosphate dosing solutions were clear, colorless and sustained the compound of formula (2) at the target concentration of 5 mg/mL over 48 hours; while consistent with the dosing solution screen, the 5 mg/mL compound of formula (2) in D2.5W with 5 mM phosphate (pH 6.0) dosing solution was clear, light yellow in appearance with only 60% recovery of the compound of formula (2) after 48 hours. Furthermore, the known degradant, the compound of formula (6), was observed in small quantities by HPLC in all samples except 5 mg/mL of the compound of formula (2) in D2.5W, 5 mM citrate (pH 5.0).

After 7 days of storage at 25° C. the non-phosphate dosing solutions were still clear and colorless in appearance. The smallest increase in acidity over the 7 days was measured for the 5 mg/mL of the compound of formula (2) in D2.5W, 5 mM citrate pH 6.0 dosing solution, while the D2.5W, 5 mM citrate pH 5.0 dosing solution had the smallest change in pH over the initial 24-48 h. Furthermore, after 14 days of storage at 25° C. the samples with dosing solution containing 5 mM citrate pH 6.0 were still clear, colorless solutions, while the dosing solutions containing either 5 mM citrate or 5 mM acetate at pH 5.0 were clear, yellow solutions. The results are summarized in Table 15.

TABLE 15

Recovery of the Compound of Formula (2) from 5 mg/mL Dosing Solutions

| Dosing Solution | Sample | Time Point | | |
|---|---|---|---|---|
| | | 0 h | 24 h | 48 h |
| (1). D2.5W, 5 mM phosphate, pH 6.0 | 1 | 101% | 100% | 60.7% |
| | 2 | 100% | 100% | 62.8% |
| (2). D2.5W, 5 mM citrate, pH 6.0 | 1 | 101% | 98.6% | 96.7% |
| | 2 | 101% | 98.8% | 96.5% |
| (3). D2.5W, 5 mM citrate, pH 5.0 | 1 | 101% | 100% | 99.1% |
| | 2 | 100% | 102% | 99.3% |
| (4). D2.5W, 5 mM acetate, pH 5.0 | 1 | 95.6% | 95.4% | 95.4% |
| | 2 | 96.0% | 96.8% | 94.8% |

It will be apparent to those in the art that specific embodiments of the disclosed subject matter may be directed to one or more of the above- and below-indicated embodiments in any combination.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound of formula (3):

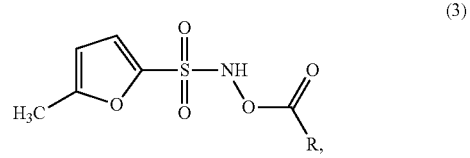

(3)

wherein
R is hydrogen, —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH$_2$, —NH—(C$_1$-C$_4$)alkyl, or —N((C$_1$-C$_4$)alkyl)$_2$,
wherein said —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with one or more substituents selected from halo, —(C$_1$-C$_6$)alkyl, —(C$_2$-C$_4$)alkenyl, —(C$_2$-C$_3$)alkynyl, -(5- or 6-membered) heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(═O)(C$_1$-C$_4$)alkyl, —C(═O)O(C$_1$-

$C_4$)alkyl, —OC(=O)($C_1$-$C_4$)alkyl, —OC(=O)$NH_2$, —S(=O)($C_1$-$C_4$)alkyl, or —S(=O)$_2$($C_1$-$C_4$)alkyl.

2. The compound of claim 1, wherein R is methyl or ethyl.
3. The compound of claim 1, wherein R is methyl.
4. The compound of claim 1, wherein R is ethyl.
5. The compound of claim 1, wherein R is benzyl or phenyl.
6. The compound of claim 1, wherein R is phenyl.
7. The compound of claim 1, wherein R is benzyl.
8. The compound of claim 1, wherein R is —$NH_2$.
9. The compound of claim 1, wherein R is unsubstituted.
10. The compound of claim 1, wherein R is substituted with a substituent selected from -halo, —$NH_2$, —$NHCH_3$, —$CF_3$, or —$OCH_3$.
11. A method of treating a cardiovascular disease, comprising administering an effective amount of the compound of claim 1 to a patient in need thereof.
12. The method of claim 11, wherein the compound is administered intravenously.
13. The method of claim 11, wherein the cardiovascular disease is heart failure.
14. The method of claim 13, wherein the compound is administered intravenously.
15. The method of claim 11, wherein the cardiovascular disease is acute decompensated heart failure.
16. The method of claim 15, wherein the compound is administered intravenously.
17. A pharmaceutical composition comprising the compound of claim 1 and at least one pharmaceutically acceptable excipient.
18. The pharmaceutical composition of claim 17, wherein the pharmaceutical composition is suitable for intravenous administration.
19. The pharmaceutical composition of claim 17, wherein the at least one pharmaceutically acceptable excipient is at least one species of cyclodextrin.
20. The pharmaceutical composition of claim 19, wherein the pharmaceutical composition is suitable for intravenous administration.
21. A method of treating a cardiovascular disease, comprising administering an effective amount of the pharmaceutical composition of claim 17 a patient in need thereof.
22. The method of claim 21, wherein the pharmaceutical composition is administered intravenously.
23. The method of claim 21, wherein the cardiovascular disease is heart failure.
24. The method of claim 23, wherein the pharmaceutical composition is administered intravenously.
25. The method of claim 21, wherein the cardiovascular disease is acute decompensated heart failure.
26. The method of claim 25, wherein the pharmaceutical composition is administered intravenously.

* * * * *